(12) United States Patent
McEvoy et al.

(10) Patent No.: US 7,378,509 B2
(45) Date of Patent: May 27, 2008

(54) NF-KAPPAB OLIGONUCLEOTIDE DECOY MOLECULES

(75) Inventors: Leslie M. McEvoy, Mountain View, CA (US); Christi Parham, Menlo Park, CA (US); Jie Zhang, Campbell, CA (US); Rolf Ehrhardt, Mill Valley, CA (US)

(73) Assignee: Anesiva, Inc., South San Francisco, CA (US)

( * ) Notice: Subject to any disclaimer, the term of this patent is extended or adjusted under 35 U.S.C. 154(b) by 0 days.

(21) Appl. No.: 11/004,512

(22) Filed: Dec. 2, 2004

(65) Prior Publication Data

US 2005/0182012 A1    Aug. 18, 2005

Related U.S. Application Data

(60) Provisional application No. 60/526,623, filed on Dec. 2, 2003, provisional application No. 60/612,029, filed on Sep. 21, 2004.

(51) Int. Cl.
    *C07H 21/04* (2006.01)

(52) U.S. Cl. .................................... 536/23.1

(58) Field of Classification Search ............... None
    See application file for complete search history.

(56) References Cited

U.S. PATENT DOCUMENTS

| | | | |
|---|---|---|---|
| 6,262,033 B1 * | 7/2001 | Morishita et al. ............. 514/44 |
| 2002/0098162 A1 | 7/2002 | Morishita et al. |
| 2003/0013669 A1 | 1/2003 | Burcoglu et al. |
| 2004/0063614 A1 | 4/2004 | Ono et al. |
| 2004/0072726 A1 | 4/2004 | Morishita et al. |
| 2004/0109843 A1 | 6/2004 | Morishita et al. |
| 2004/0138167 A1 | 7/2004 | Burcoglu et al. |
| 2004/0162250 A1 | 8/2004 | Morishita et al. |
| 2004/0162251 A1 | 8/2004 | Morishita et al. |
| 2004/0191328 A1 | 9/2004 | Warrell et al. |
| 2004/0191779 A1 | 9/2004 | Zhang et al. |
| 2005/0125054 A1 | 6/2005 | Bhat et al. |
| 2005/0175539 A1 | 8/2005 | Morishita et al. |
| 2005/0182012 A1 | 8/2005 | McEvoy et al. |
| 2005/0203612 A1 | 9/2005 | Bhat et al. |
| 2006/0057154 A1 | 3/2006 | Van Oosterhout et al. |
| 2006/0116344 A1 | 6/2006 | Morishita et al. |
| 2006/0135449 A1 | 6/2006 | Sawa et al. |
| 2006/0153847 A1 | 7/2006 | Masuda et al. |
| 2006/0241066 A1 | 10/2006 | Tomita et al. |
| 2006/0258604 A1 | 11/2006 | Strober et al. |

FOREIGN PATENT DOCUMENTS

| | | |
|---|---|---|
| EP | 0 824 918 A1 | 2/1998 |
| WO | WO 02/45659 A2 | 6/2002 |
| WO | WO 03/072038 A2 | 9/2003 |
| WO | WO 03/082331 | 10/2003 |

OTHER PUBLICATIONS

Roshak et al. (1996) J. Biol. Chem. 271:31496-31501.*
Crinelli et al., (2002) Nucleic Acids Res. 30:2435-2443.*
Faisst et al., "Compilation of Vertebrate-Encoded Transcription Factors", Nucleic Acids Research, vol. 20, No. 1, pp. 3-26, 1992.
Kunsch, Charles et al., "NF-Kappa B Subunit-Specific Regulation of the Interleukin-8 Promoter", Molecular and Cellular Biology, vol. 13, No. 10, pp. 6137-6146, Oct. 1993. (XP002329836).
Parry, Graham C. N. et al., "A Set of Inducible Genes Expressed by Activated Human Monocytic and Endothelial cells Contain kappa B-like Sites That Specifically Bind c-Rel-p65 Heterodimers", The Journal of Biochemistry, vol. 269, No. 33, pp. 20823-20825, Aug. 19, 1994. (XP002329835).
Roshak, Amy K. et al., "Manipulation of Distinct NF Kappa B Proteins Alters Inters Interleukin -1β-induced Human Rheumatoid Synoval Fibrolast Prostaglandin $E_u$ Formation", The Journal of Biological Chemistry, vol. 271, No. 49, pp. 31496-31501, 1996. (XP002329834).
Ueno et al., "Nuclear Factor-Kappa B Decoy Attenuates Neuronal Damage After Global Brain Ischemia: A Future Strategy for Brain Protection During Circulatory Arrest", The Journal of Thoracic and Cardiovascular Surgery. vol. 122, No. 4, pp. 720-727, 2001. (XP002953570).

* cited by examiner

*Primary Examiner*—J. Douglas Schultz
*Assistant Examiner*—Louis Wollenberger
(74) *Attorney, Agent, or Firm*—Christopher De Vry; Ginger R. Dreger; Goodwin Procter LLP

(57) ABSTRACT

The present invention concerns double-stranded NF-κB decoy oligodeoxynucleotide (NF-κB dsODN) molecules that contain a core sequence capable of specific binding to an NF-κB transcription factor. In a particular aspect, the invention concerns NF-κB decoy molecules that preferentially bind p50/p65 and/or cRel/p50 heterodimers over p50/p50 homodimers. In another aspect, the invention concerns NF-κB decoy molecules with improved binding affinity to p65.

23 Claims, 16 Drawing Sheets

No Treatment     Betamethasone     NF-κB Decoy

NF-κB Topical Therapy
 ¥Reduces swelling
 ¥Reduces epidermal and dermal thickening
 ¥Reduces inflammatory cell infiltrate 40x Normal     TNBS colitis     TNBS + Decoy Scatter plot of bioinformatics matrix binding score versus competition score

SEQUENCE LISTING

<160> NUMBER OF SEQ ID NOS: 93

<210> SEQ ID NO 1
<211> LENGTH: 10
<212> TYPE: DNA
<213> ORGANISM: Artificial Sequence
<220> FEATURE:
<223> OTHER INFORMATION: decoy molecule

```
<220> FEATURE:
<221> NAME/KEY: misc_feature
<222> LOCATION: 4
<223> OTHER INFORMATION: r= purine
<220> FEATURE:
<221> NAME/KEY: misc_feature
<222> LOCATION: 5-6
<223> OTHER INFORMATION: n= any base
<220> FEATURE:
<221> NAME/KEY: misc_feature
<222> LOCATION: 7-8
<223> OTHER INFORMATION: y= pyrimidine

<400> SEQUENCE: 1 gggrnnyycc                                                                 10

<210> SEQ ID NO 2
<211> LENGTH: 10
<212> TYPE: DNA
<213> ORGANISM: Artificial Sequence
<220> FEATURE:
<223> OTHER INFORMATION: decoy molecule

<400> SEQUENCE: 2
gggactttcc                                                                 10

<210> SEQ ID NO 3
<211> LENGTH: 5
<212> TYPE: DNA
<213> ORGANISM: Artificial Sequence
<220> FEATURE:
<223> OTHER INFORMATION: decoy molecule

<400> SEQUENCE: 3 gggac                                                                       5

<210> SEQ ID NO 4
<211> LENGTH: 4
<212> TYPE: DNA
<213> ORGANISM: Artificial Sequence
<220> FEATURE:
<223> OTHER INFORMATION: decoy molecule

<400> SEQUENCE: 4 ttcc                                                                        4

<210> SEQ ID NO 5
<211> LENGTH: 10
<212> TYPE: DNA
<213> ORGANISM: Artificial Sequence
<220> FEATURE:
<223> OTHER INFORMATION: decoy molecule

<400> SEQUENCE: 5
gggactttcc                                                                 10

<210> SEQ ID NO 6
<211> LENGTH: 7
<212> TYPE: DNA
<213> ORGANISM: Artificial Sequence
<220> FEATURE:
<223> OTHER INFORMATION: decoy molecule

<400> SEQUENCE: 6 ccttgaa                                                                     7

<210> SEQ ID NO 7
```

```
<211> LENGTH: 11
<212> TYPE: DNA
<213> ORGANISM: Artificial Sequence
<220> FEATURE:
<223> OTHER INFORMATION: decoy molecule

<400> SEQUENCE: 7
ggggactttc c                                                           11

<210> SEQ ID NO 8
<211> LENGTH: 3
<212> TYPE: DNA
<213> ORGANISM: Artificial Sequence
<220> FEATURE:
<223> OTHER INFORMATION: decoy molecule

<400> SEQUENCE: 8 tcc                                                                     3

<210> SEQ ID NO 9
<211> LENGTH: 12
<212> TYPE: DNA
<213> ORGANISM: Artificial Sequence
<220> FEATURE:
<223> OTHER INFORMATION: decoy molecule

<400> SEQUENCE: 9
ggggactttc cc                                                          12

<210> SEQ ID NO 10
<211> LENGTH: 20
<212> TYPE: DNA
<213> ORGANISM: Artificial Sequence
<220> FEATURE:
<223> OTHER INFORMATION: decoy molecule

<400> SEQUENCE: 10
ccttgaaggg atttccctcc                                                  20

<210> SEQ ID NO 11
<211> LENGTH: 9
<212> TYPE: DNA
<213> ORGANISM: Artificial Sequence
<220> FEATURE:
<223> OTHER INFORMATION: decoy molecule

<400> SEQUENCE: 11 gggatttcc                                                               9

<210> SEQ ID NO 12
<211> LENGTH: 2
<212> TYPE: DNA
<213> ORGANISM: Artificial Sequence
<220> FEATURE:
<223> OTHER INFORMATION: decoy molecule

<400> SEQUENCE: 12 at                                                                      2

<210> SEQ ID NO 13
<211> LENGTH: 9
<212> TYPE: DNA
<213> ORGANISM: Artificial Sequence
<220> FEATURE:
<223> OTHER INFORMATION: decoy molecule

<400> SEQUENCE: 13
```

-continued

```
ggactttcc                                                        9

<210> SEQ ID NO 14
<211> LENGTH: 2
<212> TYPE: DNA
<213> ORGANISM: Artificial Sequence
<220> FEATURE:
<223> OTHER INFORMATION: decoy molecule

<400> SEQUENCE: 14 gt                                                               2

<210> SEQ ID NO 15
<211> LENGTH: 8
<212> TYPE: DNA
<213> ORGANISM: Artificial Sequence
<220> FEATURE:
<223> OTHER INFORMATION: decoy molecule

<400> SEQUENCE: 15 gactttcc                                                         8

<210> SEQ ID NO 16
<211> LENGTH: 2
<212> TYPE: DNA
<213> ORGANISM: Artificial Sequence
<220> FEATURE:
<223> OTHER INFORMATION: decoy molecule

<400> SEQUENCE: 16 tc                                                               2

<210> SEQ ID NO 17
<211> LENGTH: 9
<212> TYPE: DNA
<213> ORGANISM: Artificial Sequence
<220> FEATURE:
<223> OTHER INFORMATION: decoy molecule

<400> SEQUENCE: 17 gactttccc                                                        9

<210> SEQ ID NO 18
<211> LENGTH: 2
<212> TYPE: DNA
<213> ORGANISM: Artificial Sequence
<220> FEATURE:
<223> OTHER INFORMATION: decoy molecule

<400> SEQUENCE: 18 tc                                                               2

<210> SEQ ID NO 19
<211> LENGTH: 8
<212> TYPE: DNA
<213> ORGANISM: Artificial Sequence
<220> FEATURE:
<223> OTHER INFORMATION: decoy molecule

<400> SEQUENCE: 19 ggatttcc                                                         8

<210> SEQ ID NO 20
<211> LENGTH: 3
<212> TYPE: DNA
```

```
<213> ORGANISM: Artificial Sequence
<220> FEATURE:
<223> OTHER INFORMATION: decoy molecule

<400> SEQUENCE: 20 ctc                                                                  3

<210> SEQ ID NO 21
<211> LENGTH: 9
<212> TYPE: DNA
<213> ORGANISM: Artificial Sequence
<220> FEATURE:
<223> OTHER INFORMATION: decoy molecule

<400> SEQUENCE: 21 ggatttccc                                                            9

<210> SEQ ID NO 22
<211> LENGTH: 3
<212> TYPE: DNA
<213> ORGANISM: Artificial Sequence
<220> FEATURE:
<223> OTHER INFORMATION: decoy molecule

<400> SEQUENCE: 22 tgt                                                                  3

<210> SEQ ID NO 23
<211> LENGTH: 7
<212> TYPE: DNA
<213> ORGANISM: Artificial Sequence
<220> FEATURE:
<223> OTHER INFORMATION: decoy molecule

<400> SEQUENCE: 23 gatttcc                                                              7

<210> SEQ ID NO 24
<211> LENGTH: 8
<212> TYPE: DNA
<213> ORGANISM: Artificial Sequence
<220> FEATURE:
<223> OTHER INFORMATION: decoy molecule

<400> SEQUENCE: 24 gatttccc                                                             8

<210> SEQ ID NO 25
<211> LENGTH: 10
<212> TYPE: DNA
<213> ORGANISM: Artificial Sequence
<220> FEATURE:
<223> OTHER INFORMATION: decoy molecule

<400> SEQUENCE: 25
ggactttccc                                                          10

<210> SEQ ID NO 26
<211> LENGTH: 15
<212> TYPE: DNA
<213> ORGANISM: Artificial Sequence
<220> FEATURE:
<223> OTHER INFORMATION: decoy molecule

<400> SEQUENCE: 26
ttgaggactt tccag                                                    15
```

```
<210> SEQ ID NO 27
<211> LENGTH: 15
<212> TYPE: DNA
<213> ORGANISM: Artificial Sequence
<220> FEATURE:
<223> OTHER INFORMATION: decoy molecule

<400> SEQUENCE: 27
ctcggacttt cctgt                                                    15

<210> SEQ ID NO 28
<211> LENGTH: 19
<212> TYPE: DNA
<213> ORGANISM: Artificial Sequence
<220> FEATURE:
<223> OTHER INFORMATION: decoy molecule

<400> SEQUENCE: 28
agttgaggga tttccaggc                                                19

<210> SEQ ID NO 29
<211> LENGTH: 20
<212> TYPE: DNA
<213> ORGANISM: Artificial Sequence
<220> FEATURE:
<223> OTHER INFORMATION: decoy molecule

<400> SEQUENCE: 29
agttgaggac tttcccaggc                                               20

<210> SEQ ID NO 30
<211> LENGTH: 19
<212> TYPE: DNA
<213> ORGANISM: Artificial Sequence
<220> FEATURE:
<223> OTHER INFORMATION: decoy molecule

<400> SEQUENCE: 30
agttgaggac tttccaggc                                                19

<210> SEQ ID NO 31
<211> LENGTH: 19
<212> TYPE: DNA
<213> ORGANISM: Artificial Sequence
<220> FEATURE:
<223> OTHER INFORMATION: decoy molecule

<400> SEQUENCE: 31
agttgaggat ttcccaggc                                                19

<210> SEQ ID NO 32
<211> LENGTH: 14
<212> TYPE: DNA
<213> ORGANISM: Artificial Sequence
<220> FEATURE:
<223> OTHER INFORMATION: decoy molecule

<400> SEQUENCE: 32
tcggactttc cctc                                                     14

<210> SEQ ID NO 33
<211> LENGTH: 13
<212> TYPE: DNA
<213> ORGANISM: Artificial Sequence
<220> FEATURE:
```

-continued

```
<223> OTHER INFORMATION: decoy molecule

<400> SEQUENCE: 33
atggactttc cgt                                                          13

<210> SEQ ID NO 34
<211> LENGTH: 12
<212> TYPE: DNA
<213> ORGANISM: Artificial Sequence
<220> FEATURE:
<223> OTHER INFORMATION: decoy molecule

<400> SEQUENCE: 34
tcggatttcc tc                                                           12

<210> SEQ ID NO 35
<211> LENGTH: 13
<212> TYPE: DNA
<213> ORGANISM: Artificial Sequence
<220> FEATURE:
<223> OTHER INFORMATION: decoy molecule

<400> SEQUENCE: 35
tcggactttc ctc                                                          13

<210> SEQ ID NO 36
<211> LENGTH: 17
<212> TYPE: DNA
<213> ORGANISM: Artificial Sequence
<220> FEATURE:
<223> OTHER INFORMATION: decoy molecule

<400> SEQUENCE: 36
ttgaggactt tccaggc                                                      17

<210> SEQ ID NO 37
<211> LENGTH: 14
<212> TYPE: DNA
<213> ORGANISM: Artificial Sequence
<220> FEATURE:
<223> OTHER INFORMATION: decoy molecule

<400> SEQUENCE: 37
tcgggacttt cctc                                                         14

<210> SEQ ID NO 38
<211> LENGTH: 18
<212> TYPE: DNA
<213> ORGANISM: Artificial Sequence
<220> FEATURE:
<223> OTHER INFORMATION: decoy molecule

<400> SEQUENCE: 38
agttgaggat ttccaggc                                                     18

<210> SEQ ID NO 39
<211> LENGTH: 18
<212> TYPE: DNA
<213> ORGANISM: Artificial Sequence
<220> FEATURE:
<223> OTHER INFORMATION: decoy molecule

<400> SEQUENCE: 39
tgaggacttt ccaggctc                                                     18
```

```
<210> SEQ ID NO 40
<211> LENGTH: 16
<212> TYPE: DNA
<213> ORGANISM: Artificial Sequence
<220> FEATURE:
<223> OTHER INFORMATION: decoy molecule

<400> SEQUENCE: 40
tgaggacttt ccaggc                                                    16

<210> SEQ ID NO 41
<211> LENGTH: 17
<212> TYPE: DNA
<213> ORGANISM: Artificial Sequence
<220> FEATURE:
<223> OTHER INFORMATION: decoy molecule

<400> SEQUENCE: 41
ttgcggactt tccaggc                                                   17

<210> SEQ ID NO 42
<211> LENGTH: 14
<212> TYPE: DNA
<213> ORGANISM: Artificial Sequence
<220> FEATURE:
<223> OTHER INFORMATION: decoy molecule

<400> SEQUENCE: 42
ctgggacttt cctc                                                      14

<210> SEQ ID NO 43
<211> LENGTH: 18
<212> TYPE: DNA
<213> ORGANISM: Artificial Sequence
<220> FEATURE:
<223> OTHER INFORMATION: decoy molecule

<400> SEQUENCE: 43
gttgagggac tttccagg                                                  18

<210> SEQ ID NO 44
<211> LENGTH: 16
<212> TYPE: DNA
<213> ORGANISM: Artificial Sequence
<220> FEATURE:
<223> OTHER INFORMATION: decoy molecule

<400> SEQUENCE: 44
ctcgggactt tcctgt                                                    16

<210> SEQ ID NO 45
<211> LENGTH: 16
<212> TYPE: DNA
<213> ORGANISM: Artificial Sequence
<220> FEATURE:
<223> OTHER INFORMATION: decoy molecule

<400> SEQUENCE: 45
tcggggactt tccctc                                                    16

<210> SEQ ID NO 46
<211> LENGTH: 19
<212> TYPE: DNA
<213> ORGANISM: Artificial Sequence
<220> FEATURE:
<223> OTHER INFORMATION: decoy molecule
```

```
<400> SEQUENCE: 46
cagtagtatg tgagcctgc                                          19

<210> SEQ ID NO 47
<211> LENGTH: 20
<212> TYPE: DNA
<213> ORGANISM: Artificial Sequence
<220> FEATURE:
<223> OTHER INFORMATION: decoy molecule

<400> SEQUENCE: 47
ttgccgtacc tgacttagcc                                         20

<210> SEQ ID NO 48
<211> LENGTH: 22
<212> TYPE: DNA
<213> ORGANISM: Artificial Sequence
<220> FEATURE:
<223> OTHER INFORMATION: decoy molecule

<400> SEQUENCE: 48
agttgagggg actttcccag gc                                      22

<210> SEQ ID NO 49
<211> LENGTH: 13
<212> TYPE: DNA
<213> ORGANISM: Artificial Sequence
<220> FEATURE:
<223> OTHER INFORMATION: decoy molecule

<400> SEQUENCE: 49
tcgggatttc ctc                                                13

<210> SEQ ID NO 50
<211> LENGTH: 20
<212> TYPE: DNA
<213> ORGANISM: Artificial Sequence
<220> FEATURE:
<223> OTHER INFORMATION: decoy molecule

<400> SEQUENCE: 50
agttgaggga ctttccaggc                                         20

<210> SEQ ID NO 51
<211> LENGTH: 18
<212> TYPE: DNA
<213> ORGANISM: Artificial Sequence
<220> FEATURE:
<223> OTHER INFORMATION: decoy molecule

<400> SEQUENCE: 51
agttgagact ttccaggc                                           18

<210> SEQ ID NO 52
<211> LENGTH: 19
<212> TYPE: DNA
<213> ORGANISM: Artificial Sequence
<220> FEATURE:
<223> OTHER INFORMATION: decoy molecule

<400> SEQUENCE: 52
agttgagact tcccaggc                                           19

<210> SEQ ID NO 53
<211> LENGTH: 9
```

```
<212> TYPE: DNA
<213> ORGANISM: Artificial Sequence
<220> FEATURE:
<223> OTHER INFORMATION: decoy molecule

<400> SEQUENCE: 53 ggactttcc                                                              9

<210> SEQ ID NO 54
<211> LENGTH: 11
<212> TYPE: DNA
<213> ORGANISM: Artificial Sequence
<220> FEATURE:
<223> OTHER INFORMATION: decoy molecule

<400> SEQUENCE: 54
aggactttcc a                                                          11

<210> SEQ ID NO 55
<211> LENGTH: 13
<212> TYPE: DNA
<213> ORGANISM: Artificial Sequence
<220> FEATURE:
<223> OTHER INFORMATION: decoy molecule

<400> SEQUENCE: 55
ctggactttc ctc                                                        13

<210> SEQ ID NO 56
<211> LENGTH: 17
<212> TYPE: DNA
<213> ORGANISM: Artificial Sequence
<220> FEATURE:
<223> OTHER INFORMATION: decoy molecule

<400> SEQUENCE: 56
aagaggactt tccagag                                                    17

<210> SEQ ID NO 57
<211> LENGTH: 17
<212> TYPE: DNA
<213> ORGANISM: Artificial Sequence
<220> FEATURE:
<223> OTHER INFORMATION: decoy molecule

<400> SEQUENCE: 57
atatggactt tccttaa                                                    17

<210> SEQ ID NO 58
<211> LENGTH: 17
<212> TYPE: DNA
<213> ORGANISM: Artificial Sequence
<220> FEATURE:
<223> OTHER INFORMATION: decoy molecule

<400> SEQUENCE: 58
caacggactt tccacac                                                    17

<210> SEQ ID NO 59
<211> LENGTH: 17
<212> TYPE: DNA
<213> ORGANISM: Artificial Sequence
<220> FEATURE:
<223> OTHER INFORMATION: decoy molecule

<400> SEQUENCE: 59
```
cagtggactt tccactg                                                         17

<210> SEQ ID NO 60
<211> LENGTH: 13
<212> TYPE: DNA
<213> ORGANISM: Artificial Sequence
<220> FEATURE:
<223> OTHER INFORMATION: decoy molecule

<400> SEQUENCE: 60
tcgactttcc ctc                                                             13

<210> SEQ ID NO 61
<211> LENGTH: 16
<212> TYPE: DNA
<213> ORGANISM: Artificial Sequence
<220> FEATURE:
<223> OTHER INFORMATION: decoy molecule

<400> SEQUENCE: 61
ctggggactt ccctc                                                           16

<210> SEQ ID NO 62
<211> LENGTH: 13
<212> TYPE: DNA
<213> ORGANISM: Artificial Sequence
<220> FEATURE:
<223> OTHER INFORMATION: decoy molecule

<400> SEQUENCE: 62
tcggatttcc ctc                                                             13

<210> SEQ ID NO 63
<211> LENGTH: 11
<212> TYPE: DNA
<213> ORGANISM: Artificial Sequence
<220> FEATURE:
<223> OTHER INFORMATION: decoy molecule

<400> SEQUENCE: 63
tcgatttcct c                                                               11

<210> SEQ ID NO 64
<211> LENGTH: 12
<212> TYPE: DNA
<213> ORGANISM: Artificial Sequence
<220> FEATURE:
<223> OTHER INFORMATION: decoy molecule

<400> SEQUENCE: 64
tcgatttccc tc                                                              12

<210> SEQ ID NO 65
<211> LENGTH: 18
<212> TYPE: DNA
<213> ORGANISM: Artificial Sequence
<220> FEATURE:
<223> OTHER INFORMATION: decoy molecule

<400> SEQUENCE: 65
ctcggggact ttccctca                                                        18

<210> SEQ ID NO 66
<211> LENGTH: 15
<212> TYPE: DNA
<213> ORGANISM: Artificial Sequence

```
<220> FEATURE:
<223> OTHER INFORMATION: decoy molecule

<400> SEQUENCE: 66
ctcggacttt cctca                                                        15

<210> SEQ ID NO 67
<211> LENGTH: 16
<212> TYPE: DNA
<213> ORGANISM: Artificial Sequence
<220> FEATURE:
<223> OTHER INFORMATION: decoy molecule

<400> SEQUENCE: 67
ttgaggattt ccaggc                                                       16

<210> SEQ ID NO 68
<211> LENGTH: 17
<212> TYPE: DNA
<213> ORGANISM: Artificial Sequence
<220> FEATURE:
<223> OTHER INFORMATION: decoy molecule

<400> SEQUENCE: 68
ttgaggattt ccaggct                                                      17

<210> SEQ ID NO 69
<211> LENGTH: 18
<212> TYPE: DNA
<213> ORGANISM: Artificial Sequence
<220> FEATURE:
<223> OTHER INFORMATION: decoy molecule

<400> SEQUENCE: 69
ttgaggattt ccaggctc                                                     18

<210> SEQ ID NO 70
<211> LENGTH: 15
<212> TYPE: DNA
<213> ORGANISM: Artificial Sequence
<220> FEATURE:
<223> OTHER INFORMATION: decoy molecule

<400> SEQUENCE: 70
tgaggacttt ccagg                                                        15

<210> SEQ ID NO 71
<211> LENGTH: 13
<212> TYPE: DNA
<213> ORGANISM: Artificial Sequence
<220> FEATURE:
<223> OTHER INFORMATION: decoy molecule

<400> SEQUENCE: 71
gaggactttc cag                                                          13

<210> SEQ ID NO 72
<211> LENGTH: 18
<212> TYPE: DNA
<213> ORGANISM: Artificial Sequence
<220> FEATURE:
<223> OTHER INFORMATION: decoy molecule

<400> SEQUENCE: 72
gttgaggact ttccaggc                                                     18
```

<210> SEQ ID NO 73
<211> LENGTH: 15
<212> TYPE: DNA
<213> ORGANISM: Artificial Sequence
<220> FEATURE:
<223> OTHER INFORMATION: decoy molecule

<400> SEQUENCE: 73
gaggactttc caggc                                                    15

<210> SEQ ID NO 74
<211> LENGTH: 14
<212> TYPE: DNA
<213> ORGANISM: Artificial Sequence
<220> FEATURE:
<223> OTHER INFORMATION: decoy molecule

<400> SEQUENCE: 74
aggactttcc aggc                                                     14

<210> SEQ ID NO 75
<211> LENGTH: 16
<212> TYPE: DNA
<213> ORGANISM: Artificial Sequence
<220> FEATURE:
<223> OTHER INFORMATION: decoy molecule

<400> SEQUENCE: 75
aggactttcc aggctc                                                   16

<210> SEQ ID NO 76
<211> LENGTH: 19
<212> TYPE: DNA
<213> ORGANISM: Artificial Sequence
<220> FEATURE:
<223> OTHER INFORMATION: decoy molecule

<400> SEQUENCE: 76
ttgaggactt tccaggctc                                                19

<210> SEQ ID NO 77
<211> LENGTH: 18
<212> TYPE: DNA
<213> ORGANISM: Artificial Sequence
<220> FEATURE:
<223> OTHER INFORMATION: decoy molecule

<400> SEQUENCE: 77
ctcggggact ttccctgt                                                 18

<210> SEQ ID NO 78
<211> LENGTH: 22
<212> TYPE: DNA
<213> ORGANISM: Artificial Sequence
<220> FEATURE:
<223> OTHER INFORMATION: NF-kB binding site

<400> SEQUENCE: 78
agttgagggg actttcccag gc                                            22

<210> SEQ ID NO 79
<211> LENGTH: 6
<212> TYPE: DNA
<213> ORGANISM: Artificial Sequence
<220> FEATURE:
<223> OTHER INFORMATION: decoy molecule

```
<400> SEQUENCE: 79 agttga                                                              6

<210> SEQ ID NO 80
<211> LENGTH: 4
<212> TYPE: DNA
<213> ORGANISM: Artificial Sequence
<220> FEATURE:
<223> OTHER INFORMATION: decoy molecule

<400> SEQUENCE: 80 ttga                                                                4

<210> SEQ ID NO 81
<211> LENGTH: 5
<212> TYPE: DNA
<213> ORGANISM: Artificial Sequence
<220> FEATURE:
<223> OTHER INFORMATION: decoy molecule

<400> SEQUENCE: 81 gttga                                                               5

<210> SEQ ID NO 82
<211> LENGTH: 3
<212> TYPE: DNA
<213> ORGANISM: Artificial Sequence
<220> FEATURE:
<223> OTHER INFORMATION: decoy molecule

<400> SEQUENCE: 82 ctc                                                                 3

<210> SEQ ID NO 83
<211> LENGTH: 3
<212> TYPE: DNA
<213> ORGANISM: Artificial Sequence
<220> FEATURE:
<223> OTHER INFORMATION: decoy molecule

<400> SEQUENCE: 83 tca                                                                 3

<210> SEQ ID NO 84
<211> LENGTH: 2
<212> TYPE: DNA
<213> ORGANISM: Artificial Sequence
<220> FEATURE:
<223> OTHER INFORMATION: decoy molecule

<400> SEQUENCE: 84 ct                                                                  2

<210> SEQ ID NO 85
<211> LENGTH: 2
<212> TYPE: DNA
<213> ORGANISM: Artificial Sequence
<220> FEATURE:
<223> OTHER INFORMATION: decoy molecule

<400> SEQUENCE: 85 tc                                                                  2

<210> SEQ ID NO 86
```

```
<211> LENGTH: 2
<212> TYPE: DNA
<213> ORGANISM: Artificial Sequence
<220> FEATURE:
<223> OTHER INFORMATION: decoy molecule

<400> SEQUENCE: 86 tc                                                                        2

<210> SEQ ID NO 87
<211> LENGTH: 2
<212> TYPE: DNA
<213> ORGANISM: Artificial Sequence
<220> FEATURE:
<223> OTHER INFORMATION: decoy molecule

<400> SEQUENCE: 87 ca                                                                        2

<210> SEQ ID NO 88
<211> LENGTH: 4
<212> TYPE: DNA
<213> ORGANISM: Artificial Sequence
<220> FEATURE:
<223> OTHER INFORMATION: decoy molecule

<400> SEQUENCE: 88 aggc                                                                      4

<210> SEQ ID NO 89
<211> LENGTH: 4
<212> TYPE: DNA
<213> ORGANISM: Artificial Sequence
<220> FEATURE:
<223> OTHER INFORMATION: decoy molecule

<400> SEQUENCE: 89 aggc                                                                      4

<210> SEQ ID NO 90
<211> LENGTH: 4
<212> TYPE: DNA
<213> ORGANISM: Artificial Sequence
<220> FEATURE:
<223> OTHER INFORMATION: decoy molecule

<400> SEQUENCE: 90 ttga                                                                      4

<210> SEQ ID NO 91
<211> LENGTH: 2
<212> TYPE: DNA
<213> ORGANISM: Artificial Sequence
<220> FEATURE:
<223> OTHER INFORMATION: decoy molecule

<400> SEQUENCE: 91 ag                                                                        2

<210> SEQ ID NO 92
<211> LENGTH: 3
<212> TYPE: DNA
<213> ORGANISM: Artificial Sequence
<220> FEATURE:
<223> OTHER INFORMATION: flanking sequence

<400> SEQUENCE: 92
```

```
agg                                                                3
```

<210> SEQ ID NO 93
<211> LENGTH: 12
<212> TYPE: PRT
<213> ORGANISM: Artificial Sequence
<220> FEATURE:
<223> OTHER INFORMATION: Nuclear localization signal containing peptide

<400> SEQUENCE: 93

Pro Lys Lys Lys Arg Lys Val Glu Asp Pro Tyr Cys
 1               5                  10

US 7,378,509 B2

NF-KAPPAB OLIGONUCLEOTIDE DECOY MOLECULES

BACKGROUND OF THE INVENTION

This application claims priority under 35 U.S.C. § 119(e)(1) of U.S. provisional patent application Ser. No. 60/526,623, filed on Dec. 2, 2003, and U.S. Provisional patent application Ser. No. 60/612,029, filed on Sep. 21, 2004, the entire disclosures of which are hereby expressly incorporated by reference.

FIELD OF THE INVENTION

The present invention concerns NF-κB oligonucleotide decoy molecules, and their use in the treatment of various NF-κB related diseases and pathological conditions.

DESCRIPTION OF THE RELATED ART

NF-κB is a family of inducible dimeric transcription factors composed of members of the Rel family of DNA-binding proteins that recognize a common sequence motif. In its active DNA-binding form, NF-κB is a heterogeneous collection of dimers, composed of various combinations of members of the NF-κB/Rel family. At present, this family is composed of 5 members, termed p52, p50, p65, cRel and Rel B. The homology between the members of the Rel family is through the Rel homology domain, which is about 300 amino acids in size and constitutes the DNA-binding domain of these proteins.

Different NF-κB dimers exhibit different binding affinities for NF-κB sites bearing the consensus sequence GGGRN-NYYCC (SEQ ID NO: 1) where R is purine, Y is pyrimidine and N is any base. The Rel proteins differ in their abilities to activate transcription, such that only p65/RelA and c-Rel were found to contain potent transcriptional-activation domains among the mammalian family members. NF-κB is found in its inactive form in the cytoplasm, where it is bound to the 43-kDa protein IκB that covers the nuclear localization signal region of the p65/p50 dimer. Activation of NF-κB starts with the proteolytic destruction of IκB followed by the transport of the RelA/p50 complex into the nucleus, where it binds to its recognition site on the DNA and activates transcription of target genes. For further review of the NFκB family see, for example, Gomez et al., *Frontiers in Bioscience* 2:49-60 (1997).

p52 and p50 do not contain transactivation domains. Dimers composed solely of p52 and/or p50 proteins that lack transcriptional activation domains are generally not activators of transcription and can mediate transcriptional repression.

The transcription factors of the Rel/NF-κB family are key regulators of immune and inflammatory responses, and contribute to lymphocyte proliferation, survival and oncogenesis. Thus, NF-κB plays a key role in the expression of several genes involved in the inflammation, cell proliferation and immune responses. (D'Acquisto et al., *Gene Therapy* 7: 1731-1737 (2000); Griesenbach et al., *Gene Therapy* 7, 306-313 (2000); Morishita et al., *Gene Therapy* 7: 1847-1852 (2000)). Among the genes regulated by NF-κB are many which play critical roles in various diseases and conditions, such as rheumatoid arthritis, systemic lupus erythematosus, restenosis, myocardial infarction, ischemia reperfusion injury, glomerulonephritis, atopic dermatitis, saphenous vein graft, Alzheimer's disease, to name a few. See, e.g. Khaled et al. *Clinical Immunology and Immunopathology* 86(2): 170-179 (1998); Morishita et al., *Nature Medicine* 3(8): 894-899 (1997); Cho-Chung et al., *Current Opinion in Molecular Therapeutics* 1(3): 386-392 (1999); Nakamura et al., *Gene Therapy* 9: 1221-1229 (2002); Shintani et al., *Ann. Thorac. Surg.* 74: 1132-1138 (2002); and Li et al., *J. Neurochem.* 74(1): 143-150 (2000).

NF-κB decoys have been proposed for the inhibition of neointimal hyperplasia after angioplasty, restenosis and myocardial infarction (Yoshimura et al., *Gene Therapy* 8: 1635-1642 (2001); Morishita et al., *Nature Medicine* 3(8): 894-899 (1997)). The greater inhibition of reperfusion injury, acute, and chronic rejection after transplantation results in a prolongation of allograft survival and decrease in graft coronary artery disease. (Feeley et al., *Transplantation* 70(11): 1560-1568 (2000)). In vivo transfection of an NFκB decoy provides a novel strategy for treatment of acute myocarditis. (Yokoseki et al., supra). Ueno et al., supra reported that blocking NFκB by NFκB decoy prevented ischemia reperfusion injury in the heart.

It has been shown (Ziegler-Heitbrock et al, *J. Leukoc. Biol.* 55(10:73-80 (1994); Kastenbauer and Ziegler-Heitbrock, *Infect. Immunol.* 67(4):1553-9 (1999)) that when a human monocyte cell line, Mono Mac 6, was pre-treated for two days with low doses of lipopolysaccharide (LPS), the response to subsequent LPS stimulation was strongly reduced. Upon stimulation of these LPS-tolerant cells with LPS, these cells exhibited a predominance of the p50 homodimer as shown by the gel shift assay. The authors then tested the effect of the altered NF-κB complexes on gene expression via reporter gene analysis. NF-κB-dependent HIV-1 LTR reporter gene constructs were transfected into Mono Mac 6 cells, followed by pre-culture with and without LPS, and luciferase activity was measured. When LPS-tolerant cells were tested, LPS stimulation did not increase transactivation of the NF-κB-dependent HIV-1 LTR reporter gene. This indicates that the NF-κB complexes present in LPS-tolerant cells are functionally inactive. This also was applicable to the transcription of the NP-κB-controlled TNF gene. Using a TNF promoter-controlled luciferase reporter construct, LPS-tolerant cells showed only a minimal response to LPS stimulation. Therefore, it was concluded that the p50 homodimers induced by LPS tolerance lack transactivation activity. These p50 homodimers instead occupy the cognate NF-κB-binding sites and prevent transactivation and therefore transcription by the p50/p65 complex.

SUMMARY OF THE INVENTION

The present invention concerns double-stranded NF-κB decoy oligodeoxynucleotide (NF-κB dsODN) molecules that contain a core sequence capable of specific binding to an NF-κB transcription factor. In a particular aspect, the invention concerns NF-κB decoy molecules that preferentially bind p50/p65 and/or cRel/p50 heterodimers over p50/p50 homodimers when p50/p50 homodimers are present. The selective decoy molecules of the invention, by not blocking p50/p50 homodimers, allow these homodimers to block the promoters of NF-κB regulated genes, which provides an additional level of negative regulation of gene transcription. As a result, the selective NF-κB decoy molecules are particularly potent inhibitors of NF-κB activity both in vitro and in vivo.

If p50/p50 homodimers are not present, are present only in small amounts, or do not play a significant role in the disease state, the invention provides NF-κB decoy molecules with high binding affinity for p65.

In one aspect, the invention concerns double-stranded NF-κB decoy oligodeoxynucleotide (NF-κB dsODN) molecules that preferentially bind p50/p65 and/or cRel/p50 heterodimers relative to p50/p50 homodimers.

In another aspect, the invention concerns an NF-κB double-stranded decoy oligodeoxynucleotide (dsODN) molecule, comprising a sense and an antisense strand, which preferentially binds p50/p65 and/or cRel/p50 heterodimers over p50/p50 homodimers when p50/p50 homodimers are present and/or exhibits a p65 binding affinity of 45 or less, as determined by measuring the molar excess required to compete at least 50% of binding of p65/p50 in an electromobility shift assay to the non-mammalian NF-κB promoter from HIV (sequence 113/114).

In yet another aspect, the invention concerns The dsODN molecule of claim 1 characterized by a specificity/affinity factor of at least about 20, where the specificity/affinity factor is determined in a competitive binding assay, and is defined as follows:

Specificity/affinity factor=$(S_{p50/p50}-S_{p65/p50})\times S_{p50/p50}/S_{p65/p50}$ where $S_{p50/p50}$ equals the molar excess of said dsODN molecule required to compete 50% of the binding of p50/p50 to the non-mammalian NF-κB promoter from HIV (sequence 113/114) and $S_{p65/p50}$ equals the molar excess of said dsODN molecule required to compete 50% of the binding of p65/p50 to the non-mammalian NF-κB promoter from HIV (sequence 113/114), and wherein the score (S) is assigned as 100 if the decoy is unable to compete at least 50% of the binding at any molar ratio tested.

In another aspect, the present invention concerns NF-κB dsODN molecules that have a specificity/affinity factor of at least about 25, or at least about 30, or at least about 35, or at least about 40, or at least about 50 or at least about 60, or at least about 70, or at least about 80. In a preferred embodiment, the decoy molecules of the invention additionally show increased binding affinity to the p50/p65 heterodimers and/or have improved stability in vivo.

In a further aspect, the invention concerns a dsODN molecule comprising in its first strand, in 5' to 3' direction, a sequence of the formula FLANK1-CORE-FLANK2, wherein CORE is selected from the group consisting of GGGATTTCC (SEQ ID NO: 11); GGACTTTCC (SEQ ID NO: 13); GGATTTCC (SEQ ID NO: 19); GGATTTCCC (SEQ ID NO: 21); and GGACTTTCCC (SEQ ID NO: 25);

FLANK1 is selected from the group consisting of AT; TC; CTC; AGTTGA (SEQ ID NO: 79), and TTGA (SEQ ID NO: 80);

FLANK2 is selected from the group consisting of GT; TC; TGT; AGGC (SEQ ID NO: 88); and AG.

In a specific embodiment, CORE is selected from the group consisting of GGGATTTCC (SEQ ID NO: 11); GGACTTTCC (SEQ ID NO: 13); and GGATTTCC (SEQ ID NO: 19); FLANK1 is AT and FLANK2 is GT; or FLANK1 is TC and FLANK2 is TC; or FLANK1 is CTC and FLANK2 is TGT; or FLANK1 is AGTTGA (SEQ ID NO: 79) and FLANK2 is AGGC (SEQ ID NO: 88); or FLANK1 is TTGA and FLANK2 is AG.

In another specific embodiment, CORE is GGGATTTCC (SEQ ID NO: 11); or GGACTTTCC (SEQ ID NO: 13); FLANK1 is (AGTTGA SEQ ID NO: 79), and FLANK 2 is AGGC (SEQ ID NO: 88).

In yet another specific embodiment, The dsODN molecule of claim 14 wherein CORE is GGACTTTCC (SEQ ID NO: 13), FLANK1 is AGTTGA (SEQ ID NO: 79) and FLANK 2 is AGGC (SEQ ID NO: 88).

The NF-κB dsODN molecules include a second strand that is at least partially complementary to said first strand, and may have a phosphodiesterate, phosphorothioate, mixed phosphodiesterate-phosphorothioate, or any other modified backbone.

The two strands may be connected to each other solely by Watson-Crick base pairing and/or by covalent bonds.

In a further aspect, the invention concerns an NF-κB dsODN molecule comprising a sequence, in 5' to 3' direction, selected from the group consisting of SEQ ID NOs 26 through 77 and 10.

In a still further aspect, the invention concerns an NF-κB dsODN molecule comprising a sequence, in 5' to 3' direction, selected from the group consisting of SEQ ID NOs: 26 through 34.

In another aspect, the invention concerns an NF-κB dsODN molecule comprising a sequence, in 5' to 3' direction, selected from the group consisting of SEQ ID NOs: 26 through 31.

In yet another aspect, the invention concerns an NF-κB dsODN molecule comprising the sequence of SEQ ID NO: 30.

In a particular embodiment, the NF-κB dsODN molecule is 12 to 28, or 14 to 24, or 14 to 22 base pairs long, and may comprise modified or unusual nucleotides.

In a further aspect, the invention concerns an NF-κB dsODN molecule which exhibits a p65 competitive binding affinity of 45 or less.

In a particular embodiment, the dsODN with good p65 binding affinity comprises in its sense strand, in 5' to 3' direction, a sequence of the formula FLANK1-CORE-FLANK2, wherein CORE is selected from the group consisting of GGG-GACTTTCCC (SEQ ID NO: 9); GGGACTTTCC (SEQ ID NO: 5); GGACTTTCCC (SEQ ID NO: 25); GGGATTTCC (SEQ ID NO: 11); and GGACTTTCC (SEQ ID NO: 13);

FLANK1 is selected from the group consisting of AGT-TGA (SEQ ID NO: 79); CTC, TC; CT; CCTTGAA; and CT; and FLANK 2 is selected from the group consisting of AGGC (SEQ ID NO: 88); TGT; TC; AGG; TCC; and TCA.

Just as in other aspects of the invention, the latter dsODN molecules may have hybrid or otherwise modified backbones, strands that are partially or fully complementary, and connected to each other, completely or partially, by Watson-Crick base pairing and/or by other covalent or non-covalent means.

In another aspect, the invention concerns a composition comprising an NF-κB double-stranded decoy oligodeoxynucleotide (dsODN) as described above. The composition may, for example, be a pharmaceutical composition.

In yet another aspect, the invention concerns a method for the treatment of an inflammatory, immune or autoimmune disease, comprising administering to a mammalian subject in need an effective amount of an NF-κB double-stranded decoy oligodeoxynucleotide (dsODN) molecule described above.

The invention further concerns a method for the treatment of cancer, comprising administering to a mammalian subject in need an effective amount of an NF-κB double-stranded decoy oligodeoxynucleotide (dsODN) molecule herein.

In a further aspect, the invention concerns a method for the treatment of reperfusion injury or restenosis, comprising administering to a mammalian subject in need an effective amount of an NF-κB double-stranded decoy oligodeoxynucleotide (dsODN) molecule herein.

In all aspects, the mammalian subject is preferably human.

DETAILED DESCRIPTION OF THE PREFERRED EMBODIMENTS

A. Definitions

Figure 1:
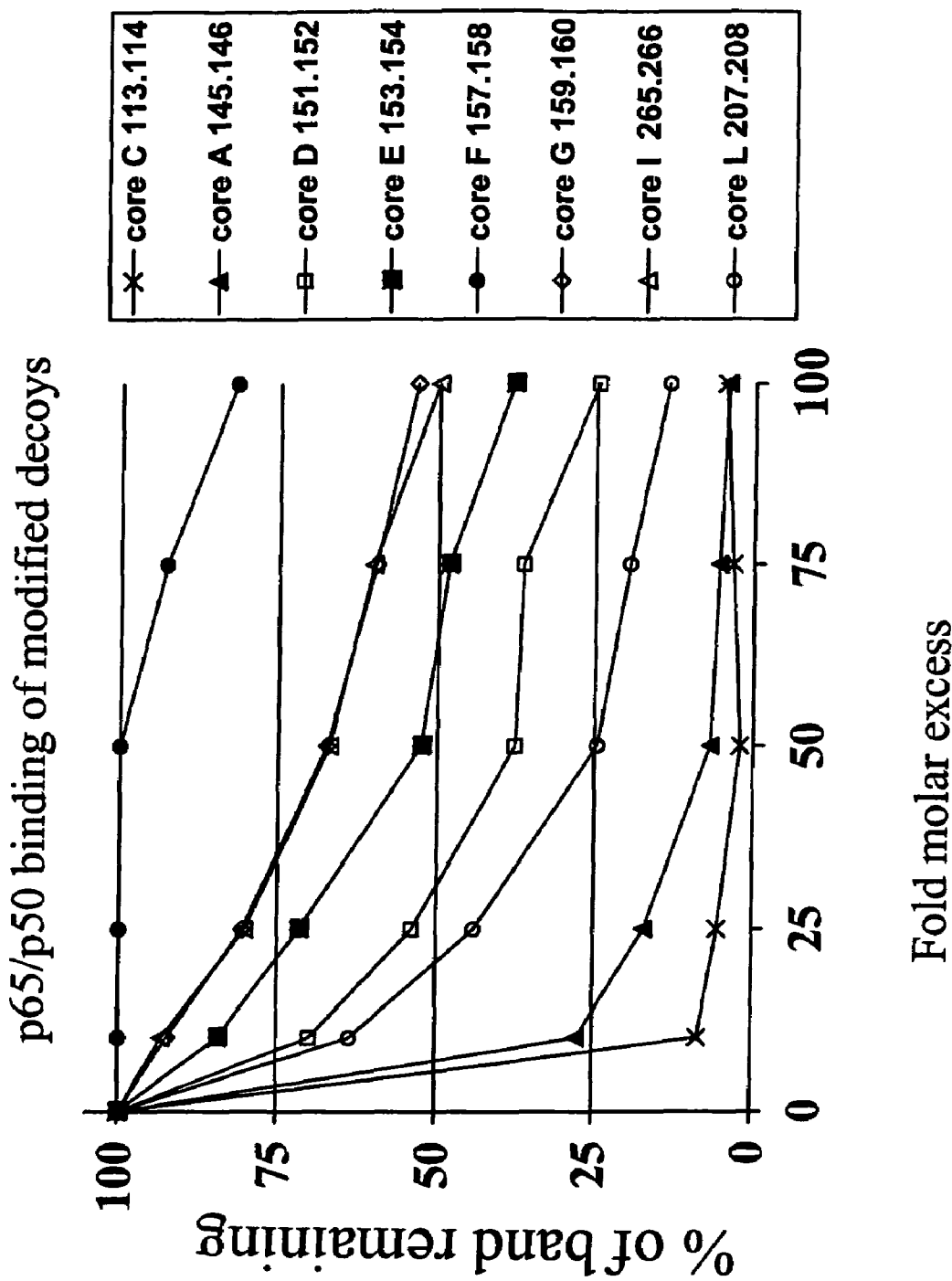
FIG. 1 is a graph showing the p65/p50 binding of certain NF-κB decoy molecules.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

The term "double-stranded" is used to refer to a nucleic acid molecule comprising two complementary nucleotide strands connected to each other solely by Watson-Crick base pairing. The term specifically includes molecules which, in addition to the double-stranded region formed by the two complementary strands, comprise single-stranded overhang(s).

The terms "oligonucleotide decoy," "double-stranded oligonucleotide decoy," "oligodeoxynucleotide decoy," and "double-stranded oligodeoxynucleotide decoy" are used interchangeably, and refer to short nucleic acid molecules comprising a double-stranded region, which bind to and interfere with a biological function of a targeted transcription factor. Accordingly, the terms "NF-κB oligonucleotide decoy," "double-stranded NF-κB oligonucleotide decoy," "NF-κB oligodeoxynucleotide decoy," and "double-stranded NF-κB oligodeoxynucleotide decoy" are used interchangeably, and refer to short nucleic acid molecules comprising a double-stranded region, which bind to and interfere with a biological function of an NF-κB transcription factor. The term "double-stranded" is used to refer to a nucleic acid molecule comprising two complementary nucleotide strands connected to each other by Watson-Crick base pairing. The term specifically includes NF-κB oligodeoxynucleotide decoy molecules which, in addition to the double-stranded region formed by the two complementary strands, comprise single-stranded overhang(s). In addition, the term specifically includes NF-κB oligodeoxynucleotide decoy molecules in which, in addition to the double-stranded region, the two strands are covalently linked to each other at their 3' and/or 5' end.

The term "NF-κB" is used herein in the broadest sense and includes all naturally occurring NF-κB molecules of any animal species, including all combinations of members of the NF-κB/Rel family, e.g. p52, p50, p65, cRel and Rel B.

The term "transcription factor binding sequence" is a short nucleotide sequence to which a transcription factor binds. The term specifically includes naturally occurring binding sequences typically found in the regulatory regions of genes the transcription of which is regulated by one or more transcription factors. The term further includes artificial (synthetic) sequences, which do not occur in nature but are capable of competitively inhibiting the binding of the transcription factor to a binding site in an endogenous gene.

As used herein, the phrase "modified nucleotide" refers to nucleotides or nucleotide triphosphates that differ in composition and/or structure from natural nucleotides and nucleotide triphosphates.

As used herein, the terms "five prime" or "5'" and "three-prime" or "3'" refer to a specific orientation as related to a nucleic acid. Nucleic acids have a distinct chemical orientation such that their two ends are distinguished as either five-prime (5') or three-prime (3'). The 3' end of a nucleic acid contains a free hydroxyl group attached to the 3' carbon of the terminal pentose sugar. The 5' end of a nucleic acid contains a free hydroxyl or phosphate group attached to the 5' carbon of the terminal pentose sugar.

As used herein, the term "overhang" refers to a double-stranded nucleic acid molecule, which does not have blunt ends, such that the ends of the two strands are not coextensive, and such that the 5' end of one strand extends beyond the 3' end of the opposing complementary strand. It is possible for a linear nucleic acid molecule to have zero, one, or two, 5' overhangs.

As used herein, the terms "preferential binding," "preferentially bind" and their grammatical equivalents are used to mean that the specificity/affinity factor is at least about 20, or at least about 25, or at least about 30, or at least about 35, or at least about 40, where the specificity/affinity ratio is defined as follows:

Specificity/affinity factor=$(S_{p50/p50}-S_{p65/p50}) \times S_{p50/p50}/S_{p65/p50}$ where $S_{p50/p50}$ equals the molar excess of decoy required to compete 50% of the binding of p50/p50 to the non-mammalian NF-κB promoter from HIV (sequence 113/114, SEQ ID NO: 48, and its complement) and $S_{p65/p50}$ equals the molar excess of decoy required to compete 50% of the binding of p65/p50 to the non-mammalian NF-κB promoter from HIV (sequence 113/114). The score (S) is assigned as 100 if the decoy is unable to compete at least 50% of the binding at any molar ratio tested.

The term "binding affinity" refers to how tightly a given transcription factor will bind to a corresponding oligonucleotide decoy, which can be measured by various experimental approaches, including electromobility shift assays (EMSA) or TransAM assays.

The term "competition ratio" describes the ability of a test decoy sequence to compete with a defined sequence for binding and retention of the transcription factor when compared to the defined sequence competing with itself in the TransAm assay. A smaller ratio refer to a higher competition ability to bind the transcription factor.

As used herein, the term "inflammatory disease" or "inflammatory disorder" refers to pathological states resulting in inflammation, typically caused by neutrophil chemotaxis. Examples of such disorders include inflammatory skin diseases including psoriasis, eczema and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include, without limitation, inflammatory skin conditions, such as dermatitis, eczema, rheumatoid arthritis (RA), rheumatoid spondylitis, gouty arthritis and other arthritic conditions, chronic inflammation, autoimmune diabetes, multiple sclerosis (MS), asthma, systhemic lupus erythrematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis, along with any disease or disorder that relates to inflammation and related disorders.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis.

The terms "cancer" and "cancerous" refer to or describe the physiological condition in mammals that is typically characterized by unregulated cell growth. Examples of cancer include, without limitation, carcinoma, lymphoma, leukemia, blastoma, and sarcoma. Specific examples of such cancers include squamous cell carcinoma, small-cell lung cancer, non-small cell lung cancer, breast cancer, pancreatic cancer, glioblastoma multiforme, cervical cancer, stomach cancer, bladder cancer, hepatoma, colon carcinoma, and head and neck cancer. In a preferred embodiment, the cancer includes breast cancer, ovarian cancer, prostate cancer, and lung cancer.

The term "treatment" refers to both therapeutic treatment and prophylactic or preventative measures, wherein the object is to prevent or slow down (lessen) the targeted pathologic condition or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

A "subject" is a vertebrate, preferably a mammal, more preferably a human.

The term "mammal" is used herein to refer to any animal classified as a mammal, including, without limitation, humans, higher primates, rodents, domestic and farm animals, and zoo, sports, or pet animals, such as sheep, dogs, horses, cats, cows, etc. Preferably, the mammal herein is human.

B. Detailed Description

It is known that the p50/p50 homodimer blocks activation of pro-inflammatory genes, while the p65/p50 heterodimer acts by turning on pro-inflammatory genes, and as a result, is a major component in the pathogenesis of inflammation. One idea underlying the present invention is that by designing decoy molecules which could bind p65/p50 and/or cRel/p50 heterodimers and not p50/p50 homodimers, or which would preferentially bind p65/p50 and/or cRel/p50 heterodimers, one could provide extra blockade of NF-κB driven promoters by leaving p50/p50 homodimers behind to occupy these sites. As a result, such selective decoy molecules have the potential to block NF-κB activity, such a pro-inflammatory activity associated with the NF-κB pathway, more efficiently than NF-κB decoys known in the art.

Another objective of the present invention is to provide NF-κB decoy molecules with improved binding affinity for p65. This class of NF-κB dsODN molecules is particularly useful in situations where p50/p50 homodimers are present in small concentrations only, like in the case of dermatitis, and therefore p65/p50 specificity is not critical.

Design of NF-κB Decoys with Improved Properties

1. Design of NF-κB dsODN Molecules

The oligonucleotide decoys of the present invention have been designed taking advantage of the crystal structure of the p50/p65 heterodimer bound to the immunoglobulin light-chain gene (Chen et al, *Nature* 391(6665):410-3 (1998)) which contains the consensus sequence of 5'-GG-GACTTTCC-3' (SEQ ID NO: 2). The authors showed that p50 contacts the 5-base-pair subsite 5'-GGGAC-3' (SEQ ID NO: 3) and that p65 contacts the 4-base-pair subsite 5'TTCC-3' (SEQ ID NO: 4). The DNA contacts by the p50/p65 heterodimer are similar to those in the homodimer structures (Ghosh et al, *Nature* 373(6512):303-10 (1995); Muller et al, *FEBS Lett.* 369(1):113-7 (1995)).

Figure 14:
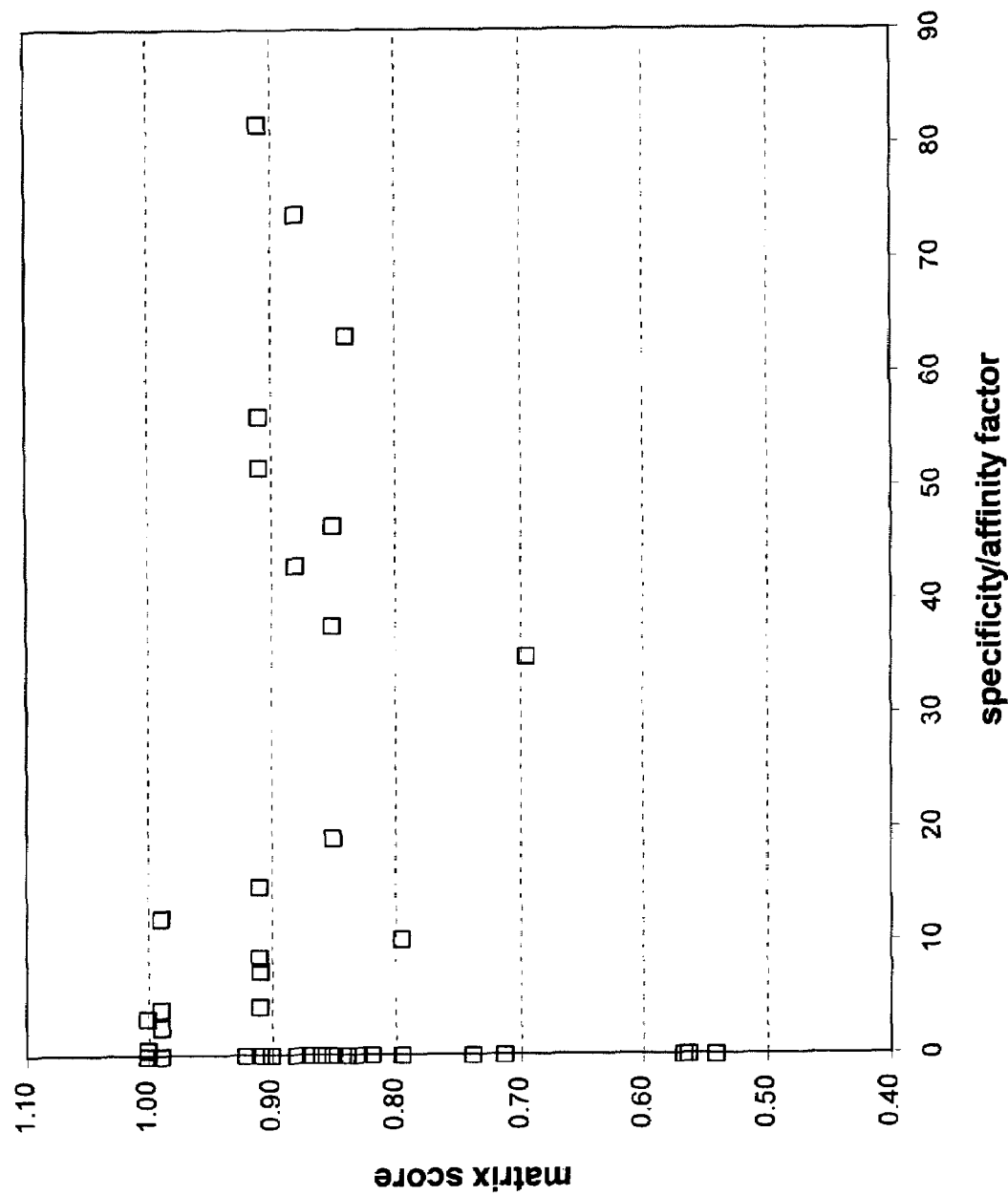
FIG. 14 shows the relationship of NF-κB affinity of various decoy molecules as predicted by bioinformatics versus the specificity/affinity factor experimentally generated.
Figure 15:
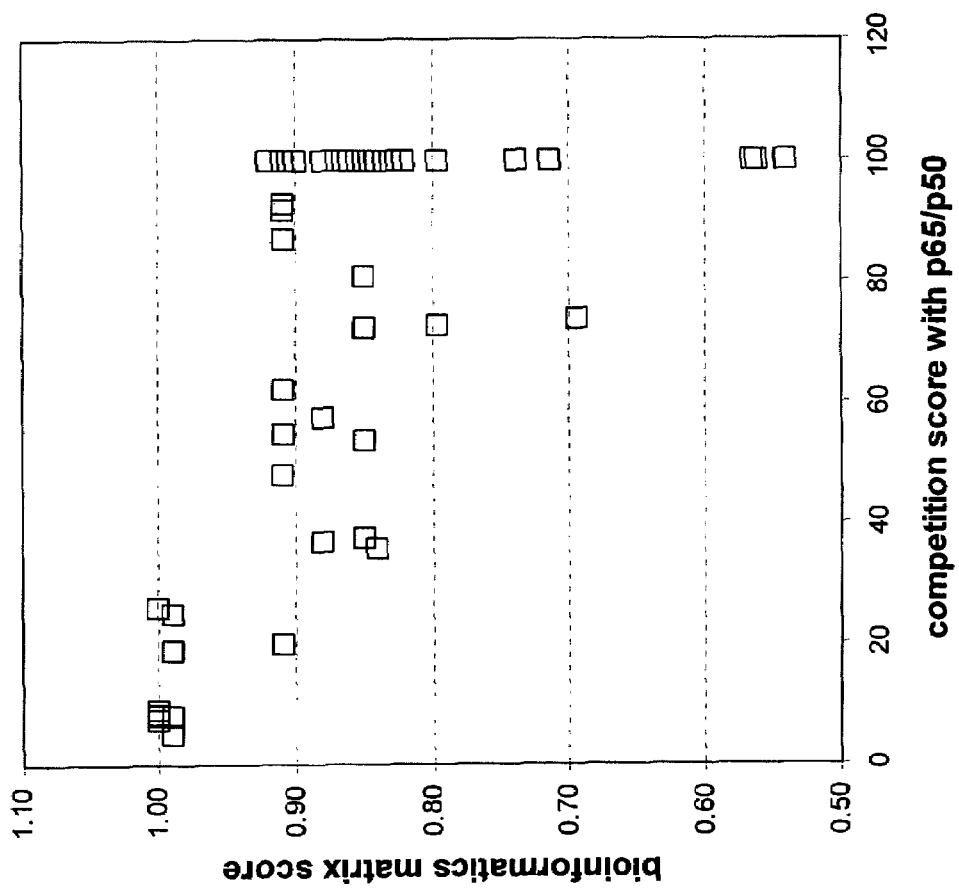
FIG. 15 is a scatter plot of bioinformatics matrix binding score versus competition score when binding to p65/p50. Lower competition scores imply higher binding affinity.
Figure 16:
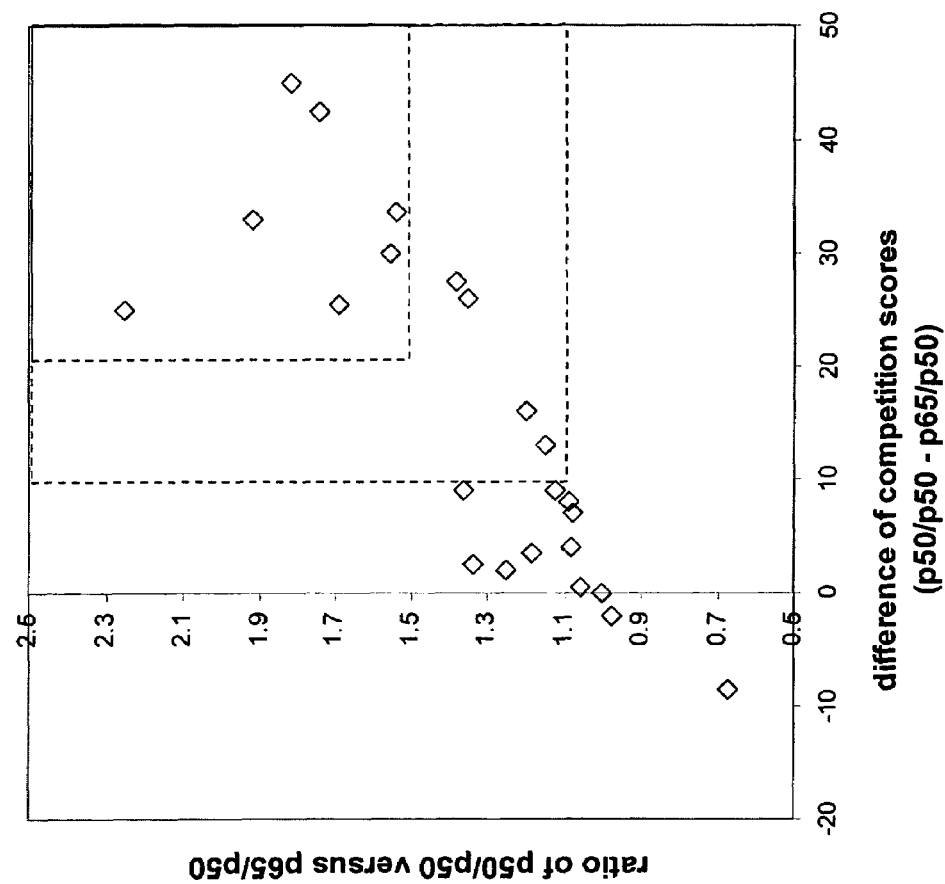
FIG. 16 is a scatter plot of the difference of competition scores between binding with p50/p50 and binding with p65/p50, versus the ratio of the competition scores (p50/p50 versus p65/p50). The plots within the smaller square represent the decoys with the best specificity for p65/p50 vs. p50/p50, whereas the plots outside the smaller and larger square have poor specificity, and the plots between (outside the smaller square and inside the larger square) have intermediate specificity.

In addition, each dsODN sequence was analyzed, using bioinformatics methods which give a score of how well a decoy is predicted to bind to NF-κB. Subsequently, the specificity/affinity factor was experimentally generated using traditional binding assays (e.g. competitive binding assay), but could easily be derived from alternative binding assays, including the TransAM™ method (Active Motif, Carlsbad, Calif.), which is an ELISA-based method for detecting and quantifying transcription factor activation. The predicted binding affinity was derived using a conventional approach to assess the TF binding affinity, using the TF binding sites matrix system that statistically summarized the experimental TF-DNA binding data. The analysis was conducted using the most updated version (8.2, June 2004) of the TRANSFAC database (Wingender et al., *Nucleic Acids Res* 24:238-41 (1996); Wingender et al., *Pac Symp Biocomput* 477-85 (1997); Wingender et al., *Nucleic Acids Res.* 25:265-8 (1997)). TRANSFAC collects position-weight-matrices for DNA-TF binding. The tool Match (Kel et al., *Nucleic Acids Res.* 31:3576-9 (2003)) was used to assess the binding affinity of decoys using the matrices of TRANSFAC, and actual specificity/affinity factors were compared. The data are illustrated in FIGS. 14 and 15, and discussed below. The exact scores will be assay dependent, however, the relative affinity would remain valid, regardless of the specific assay used.

In one embodiment, the NF-κB dsODN molecules of the present invention consist of two oligonucleotide strands which are attached to each other by Watson-Crick base pairing. While typically all nucleotides in the two strands participate in the base pairing, this is not a requirement. Oligonucleotide decoy molecules, where one or more, such as 1-3 or 1 or 2 nucleotides are not involved in base pairing are also included. In addition, the double stranded decoys may contain 3' and/or 5' single stranded overhangs.

In another embodiment, the NF-κB dsODN molecules of the present invention comprise two oligonucleotide strands which are attached to each other by Watson-Crick base pairing, and are additionally covalently attached to each other at either the 3' or the 5' end, or both, resulting in a dumbell structure, or a circular molecule. The covalent linkage may be provided, for example, by phosphodiester linkages or other linking groups, such as, for example, phosphothioate, phosphodithioate, or phosphoamidate linkages.

Generally, the dsODN molecules of the invention comprise a core sequence that is capable of specific binding to an NF-κB transcription factor, flanked by 5' and/or 3' sequences, wherein the core sequence typically consists of about 5 to 14, or about 6 to 12, or about 7 to about 10 base pairs; and the flanking sequences are about 2 to 8, or about 2 to 6, or about 2 to 4, or about 4 to 8, or about 4 to 6 base pairs long. The molecule typically comprises an about 12 to 28, preferably about 14 to 24 base-pair long double-stranded region composed of two fully or partially complementary strands (including the core and flaking sequences).

Changing the core sequence (including its length, sequence, base modifications and backbone structure) it is possible to change the binding affinity, the stability and the specificity of the NF-κB decoy molecule. Indeed, the NF-κB dsODN molecules of the present invention, which bind the p65/p50 and/or cRel/p50 heterodimers with high affinity and exhibit no or only low affinity binding for the p50/p50 homodimers, were designed by deleting or changing targeted residues in the binding site (core) of a consensus oligonucleotide decoy, based on the crystal structure of the p65/p50 heterodimer binding to DNA, and follow up testing.

In addition, changes in the flanking sequence have a genuine impact on and can significantly increase the in vivo stability of the NF-κB decoy molecule, and may affect binding affinity and/or specificity. In particular, the shape/structure of the NF-κB decoy molecule can be changed by changing the sequences flaking the core binding sequence, which can result in improved stability and/or binding affinity. The shape and structure of the DNA are influenced by the base pair sequence, length of the DNA, backbone and nature of the nucleotide (i.e. native DNA vs. modified sugars or bases). Thus, the shape and/or structure of the molecule can also be changed by other approaches, such as, for example, by changing the total length, the length of the fully complementary, double-stranded region within the molecule, by alterations within the core and flanking sequences, by changing the backbone structure and by base modifications.

The nucleotide sequences present in the decoy molecules of the present invention may comprise modified or unusual nucleotides, and may have alternative backbone chemistries. Synthetic nucleotides may be modified in a variety of ways, see, e.g. Bielinska et al. *Science* 250:997-1000 (1990). Thus, oxygens may be substituted with nitrogen, sulfur or carbon; phosphorus substituted with carbon; deoxyribose substituted with other sugars, or individual bases substituted with an unnatural base. Thus replacement of non-bridging oxygen atoms of the internucleotide linkage with a sulfur group (to yield a phosphorothioate linkage) has been useful in increasing the nuclease resistance of the dsODN molecule. Experiments determining the relationship between the number of sulfur modifications and stability and specificity of the NF-κB dsODN molecules herein are set forth in the Example below.

In each case, any change will be evaluated as to the effect of the modification on the binding ability and affinity of the oligonucleotide decoy to the NF-κB transcription factor, effect on melting temperature and in vivo stability, as well as any deleterious physiological effects. Such modifications are well known in the art and have found wide application for anti-sense oligonucleotide, therefore, their safety and retention of binding affinity are well established (see, e.g. Wagner et al. *Science* 260:1510-1513 (1993)).

Examples of modified nucleotides, without limitation, are: 4-acetylcytidin, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, β,D-galactosylqueuosine, 2'-O-methylguanosine, inosine, N6-isopentenyladenosine 1-metyladenosine, 1-methylpseudouridine, 1-methylguanosine, 1-methylinosine, 2,2-dimethylguanosine, 2-methyladenosine, 2-methylguanosine 3-methylcytidine 5-methylcytidine, N6-methyladenosine, 7-methylguanosine, 5-methylaminomethyl-2-thiouridine, β,D-mannosylqueosine, 5-methoxycarbonylmethyl-2-thiouridine, 5-metoxycarbonalmethyluridine, 5-methoxyuridine, 2-methylthio-N6-isopentenyladenosine, N-((9-beta-D-ribofuransyl-2-methylthiopurine-6-yl)carbamoyl)threonine, N-((9-beta-D-ribofuranosyl)purine-6-yl)N-methylcarbamoyl)threonine, uridine-5-oxyacetic acid-methylester uridine-5-oxyacetic acid, wybutoxosine, pseudouridine queuosine, 2-thiocytidine, 5-methyl-2-thiouridine, 2-thiouridine, 4-thiouridine, 5-methyluridine, N-((9-beta-D-ribofuranosylpurine-6-yl)-carbamoylthreonine, 2'-O-methyl-5-methyluridine, 2'-O-methyluridine, 3-(3-3-amino-3-carboxy-propyl)uridine(acp3)u, and wybutosine.

In addition, the nucleotides can be linked to each other, for example, by a phosphoramidate linkage. This linkage is an analog of the natural phosphodiester linkage such that a bridging oxygen (—O—) is replaced with an amino group (—NR—), wherein R typically is hydrogen or a lower alkyl group, such as, for example, methyl or ethyl. Other likages, such as phosphothioate, phosphodithioate, etc. are also possible.

The decoys of the present invention can also contain modified or analogous forms of the ribose or deoxyribose sugars generally present in polynucleotide structures. Such modifications include, without limitation, 2'-substituted sugars, such as 2'-O-methyl-, 2'-O-allyl, 2'-fluoro- and 2'azido-ribose, carboxylic sugar analogs, α-anomeric sugars, epimeric sugars, such as arabinose, xyloses, lyxoses, pyranose sugars, furanose sugars, sedoheptuloses, acyclic analogs and abasic nucleoside analogs, such as methyl riboside.

In general, the oligonucleotide decoys of the present invention are preferably comprised of greater than about 50%, more preferably greater than about 80%, most preferably greater than about 90% conventional deoxyribose nucleotides.

The NF-κB dsODN decoys of the present invention can be further modified to facilitate their localization, purification, or improve certain properties thereof. For example, a nuclear localization signal (NLS) can be attached to the decoy molecules, in order to improve their delivery to the cell nucleus. The NF-κB/Rel proteins include a common Rel homology domain, which encompasses the NLS. In a preferred embodiment such naturally occurring NLS, or a variant thereof, is used in the decoy molecules of the present invention.

In addition, the NF-κB decoy molecules of the invention may be conjugated with carrier molecules, such as peptides, proteins or other types of molecules, as described, for example, in the following references: Avrameas et al., *J Autoimmun* 16, 383-391 (2001); Avrameas et al., *Bioconjug. Chem.* 10: 87-93 (1999); Gallazzi et al., *Bioconjug. Chem.* 14, 1083-1095 (2003); Ritter, W. et al., *J. Mol. Med.* 81, 708-717 (2003).

The NF-κB decoy molecules of the invention may further be derivatized to include delivery vehicles which improve delivery, distribution, target specific cell types or facilitate transit through cellular barriers. Such delivery vehicles include, without limitation, cell penetration enhancers, liposomes, lipofectin, dendrimers, DNA intercalators, and nanoparticles.

2. Synthesis of NF-κB dsODN Molecules

The NF-κB sdODN decoy molecules of the present invention can be synthesized by standard phosphodiester or phosphoramidate chemistry, using commercially available automatic synthesizers. The specific dsODN molecules described in the Examples have been synthesized using an automated DNA synthesizer (Model 380B; Applied Biosystems, Inc., Foster City, Calif.). The decoys were purified by column chromatography, lyophilized, and dissolved in culture medium. Concentrations of each decoy were determined spectrophotometrically.

3. Characterization of NF-κB dsODN Molecules

The NF-κB decoy molecules of the present invention can be conveniently tested and characterized in a gel shift, or electrophoretic mobility shift (EMSA) assay. This assay provides a rapid and sensitive method for detecting the binding of transcription factors to DNA. The assay is based on the observation that complexes of protein and DNA migrate through a non-denaturing polyacryamide gel more slowly than free double-stranded oligonucleotides. The gel shift assay is performed by incubating a purified protein, or a complex mixture of proteins (such as nuclear extracts), with a $^{32}P$ end-labeled DNA fragment containing a transcription factor-binding site. The reaction products are then analyzed on a non-denaturing polyacrylamide gel. The specificity of the transcription factor for the binding site is established by competition experiments, using excess amounts of oligonucleotides either containing a binding site for the protein of interest or a scrambled DNA sequence. The identity of proteins contained within a complex is established by using an antibody which recognizes the protein and then looking for either reduced mobility of the DNA-protein-antibody complex or disruption of the binding of this complex to the radiolabeled oligonucleotide probe.

The ability of a NF-κB decoy to bind to and block the activity of an NF-κB transcription factor can be determined in traditional binding assays (e.g. competitive binding assay), including the TransAM™ method (Active Motif, Carlsbad, Calif.), which is an ELISA-based method for detecting and quantifying transcription factor activation. Briefly, a target sequence, in this case a natural NF-κB binding site, is immobilized on the plate, and a nuclear extract containing NF-κB is incubated in the wells, in the presence or absence of decoy at various concentrations calculated as the molar ration of decoy:plate bound sequence. Positive control wells include decoy with the same sequence as the target DNA on the plate. The data obtained are presented as the ratio of the absorbance of the test decoys and the absorbance of the positive control decoy. Accordingly, lower ratios represent better binding.

In designing the selective NF-κB decoys herein, based on the crystal structure of p65/p50 heterodimer binding to DNA, targeted residues in the binding site (core) of the consensus oligonucleotide decoy were deleted. The ultimate goal was to design a double-stranded oligonucleotide which was able to bind p65/p50 and/or cRel/p50 heterodimers, preferably both the p65/p50 and cRel/p50 heterodimers, with high affinity and exhibited low affinity for p50/p50 homodimers. To achieve this aim, a variety of NF-κB decoys were tested for their ability to bind the different NF-κB proteins in a gel shift assay as described in the following Example 1.

4. Use of NF-κB dsODN Molecules, and Treatment Methods

NF-κB is involved in the regulation of the transcription of numerous genes. A representative grouping and listing of genes transcriptionally activated by NF-κB is provided below.

Cytokines/chemokines and their modulators, such as, for example, interferon-γ (IFN-γ), interferon-β (IFN-β), interleukins, such as, IL-1, Il-2, IL-6, IL-8, IL-9, IL-10, IL-11, IL-12, IL-13, IL-15, lymphotoxin-α, lymphotoxin-β, TNF-α, MIP-1, MIP-2, MIP-3, RANTES, TNF-α, TRAIL.

Immunoregulators, such as, for example, BRL-1, CCR5, CCR7, CD137, CD154, CD40 and CD40 ligand, CD48, CD83, CD23, IL-2 receptor α chain, certain immunoglobulin heavy and light chains, MHC Class I antigen, T cell receptor subunits, TNF-receptor (p75/80).

Proteins involved in antigen presentation, such as, for example, Complement B, Complement component 3, TAP1, and tapasin.

Cell adhesion molecules, such as, for example, E- and P-selectin, ICAM-1, MadCAM-1, VCAM-1, and Tenascin-C.

Acute phase proteins, such as, for example, angiotensinogen, β-defensin-2, complement factors, tissue factor-1 (TF-1), urokinase-type plasminogen activator.

Stress response genes, such as, for example, angiotensin-2, COX-2, MAP4K1, Phospholipase A2.

Cell surface receptors, such as, for example, CD23, CD69, EGF-R, Lox-1, Mdr1.

Regulators of apoptosis, such as, for example, Bfl1, Bcl-xL, Caspase-11, CD95 (Fas), TRAF-1, TRAF-2.

Growth factors and their modulators, such as, for example, G-CSF, GM-CSF, EPO, IGFBP-1, IGFBP-2, M-CSF, VEGF-C.

Early response genes, such as, for example, TIEG, B94, Egr-1.

In addition, NF-κB regulates the transcription of other transcription factors, such as c-myc-, c-myb, A20, junB, p53, WT1, and viruses.

Thus, inhibition of NF-κB induced gene expression, including expression of pro-inflammatory cytokines, such as IL-1 and TNF-α, and immune modulators, by the NF-κB decoy molecules herein is useful in the prevention and treatment of inflammatory, immune and autoimmune diseases, such as rheumatoid arthritis (RA) (Roshak et al., Current Opinion in Pharmacology 2:316-321 (2002)); Crohn's disease and inflammatory bowel disease (IBD) (Dijkstra et al., Scandinavian J. of Gastroenterology Suppl. 236:37-41 (2002)); colitis; pancreatitis (Eeber and Adler, Pancreatology 1:356-362 (2001)), periodonitis (Nichols et al., Annals of Periodontology 6:20-29 (2001)); lupus (Kammer and Tsokos, Current Directions in Autoimmunity 5:131-150 (2002)); asthma (Pahl and Szelenyi, Inflammation Research 51:273-282 (2002)); and ocular allergy (Bielory et al., Opinion in Allergy and Clinical Immunology 2:435-445 (2003)), inflammatory skin diseases, such as atopic dermatitis/eczema, psoriasis, and the like.

A more detailed list of diseases and pathogenic conditions, which are targeted for prevention and/or treatment by the NF-κB decoys of the present invention includes psoriasis, eczema and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis, and the like.

Rheumatoid Arthritis

Rheumatoid arthritis (RA) is a chronic systemic autoimmune inflammatory disease that mainly involves the synovial membrane of multiple joints with resultant injury to the articular cartilage. Efficacy of the NF-κB decoy molecules of the present invention in the prevention and/or treatment of arthritis can be evaluated in a collagen-induced arthritis (CIA) model (Terato et al. Brit. J. Rheum. 35:828-838 (1966)), in the adjuvant-induced arthritis model (Taurog et al., Cell Immunol 75:271-82 (1983); Taurog et al., Cell Immunol 80:198-204 (1983)), or a model of antibody-mediated arthritis induced by the intravenous injection of a cocktail of four monoclonal antibodies, as described by Terato et al., J. Immunol. 148:2103-8 (1992); Terato et al., Autoimmunity 22:137-47 (1995). Candidates for the prevention and/or treatment of arthritis can also be studied in transgenic animal models, such as, for example, TNF-α transgenic mice (Taconic). These animals express human tumor necrosis factor (TNF-α), a cytokine which has been implicated in the pathogenesis of human rheumatoid arthritis. The expression of TNF-α in these mice results in severe chronic arthritis of the forepaws and hind paws, and provides a good mouse model for study of inflammatory arthritis. As shown in Examples 7 and 8, a representative NF-κB decoy molecule of the present invention showed significant efficacy in the collagen-induced and adjuvant-induced arthritis models.

Skin Diseases and Related Conditions

The efficacy of the NF-κB decoy molecules of the present invention can be tested in various animal models of inflammatory skin conditions. Such models are well known in the art and include Dustmite Ag (Dp) induced contact dermatitis in NC/Nga mice (Sasakawa, T et al., Int Arch Allergy Immunol 126:239-47 (2001); Sasakawa et al., Int Arch Allergy Immunol 133:55-63 (2004)). Results of testing a representative NF-κB decoy of the invention in this model are described in Examples 3, 4, and 6.

Since porcine skin is more similar to human skin than rodent skin, the NF-κB decoy molecules of the present invention can also be tested for efficacy in the treatment of inflammatory skin conditions, such as, for example, dermatitis, and eczema in pig skin inflammatory models. The NF-κB decoy molecules of the present invention effectively block NF-κB activity in this model, and block expression of key inflammatory genes.

Existing therapies for the treatment of these conditions are inadequate, raising serious issues of side effects during long term application, especially in children. The NF-κB decoys are devoid of the known side effects of steroid therapy and involve limited systemic exposure.

Skin is known for its functional role as a protective barrier. It is now clear that skin is also a very dynamic organ that can elicit immunological responses. However, not all immunological reactions in the skin are beneficial, some harmful reaction (inflammation) might result from reacting to invaders, such as allergens (contact dermatitis, atopic dermatitis an other kin inflammatory diseases) that require down-regulation/medication. Other reactions might occur from autoreactive lymphocytes being exposed to skin antigens, such as epithelia base membrane component type VII collage or cell surface components or keratinocytes, or still unknown cell components, which can lead to pemphigus vulgaris (Anhalt et al., *N. Engl. J. Med.* 323(25):1729-35 (1990)), or epidermyosis bullosa (Woodley et al., *N. Engl. J Med.* 310(16):107-13 (1984)), or psoriasis (Stem, *Lancet* 350(9074):349-53 (1997)). Most of these inflammatory skin responses involve mononuclear cells, in particular T cells. Observations of peri- and intrafollicular inflammation and infiltration of these follicles by T cells and other immune cells, such as macrophages and dendritic cells, point to a T cell mediated autoimmune syndrome in alopecia areata (AA) as well (McElwee et al., *J. Invest. Dermatol.* 119(6): 1426-33 (2002)).

A number of studies have demonstrated the crucial role of cytokines released from immune cells infiltrating the affected sites for initiating and maintaining fibrosis in the skin of scleroderma patients (Fagundus et al., *Clin. Dermatol.* 12(3):407-17 (1994); Postlethwaite, *Current Opin. Rheumatol.* 7(6):535-40 (1995)). Thus, drugs that target immune competent cells, such as T cells, should be very successful in treating a broad spectrum of inflammatory conditions of the skin.

Inflammatory Bowel Disease (IBD)

The term "inflammatory bowel disease" or "IBD" is commonly used to ulcerative colitis and Crohn's disease, which are chronic inflammatory diseases of the gastrointestinal tract of unknown etiology. Traditional treatment is based on corticosteroid therapy and the administration of salazopyrine. More recently, other therapeutics, such as an anti-TNF-α antibody, have been developed. However, there is a great need for new therapies, partly due to the known side effects of steroid therapy, and since in a significant subgroup of patients current therapies fail to induce remission. See, e.g. Mee et al., *Gut* 2:1-5 (1979). Mouse models are described by Matsumoto, et al, *Gut* 43:71-78 (1998); and Strober et al., *J Clin Invest* 107:667-670 (2001).

Similarly to certain skin diseases, inflammatory disease of the gastrointestinal tract involves immune competent cells. For example, in inflammatory bowel disease (ulcerative colitis and Crohn's disease), T cells are the main culprit of the inflammation. The balance between pro- and anti-inflammatory cytokines secreted by T cells regulates both the initiation and perpetuation of inflammatory bowel disease. Most of these secreted factors are regulated directly or indirectly by NF-κB (Neurath et al., *Natl. Med.* 8(6):567-73 (2002); Strober et al., *J. Gastroenterol.* 38 Suppl 15:55-8 (2003)). Other diseases of the gastrointestinal tract, such as irritable bowel disease (IBS), gastritis, Barrett syndrome, peptide lulcer, reflux disease, acute and chronic pancreatitis, cholecystitis, result from similar, albeit more chronic dysregulated mucosal immune systems and thus are expected to be responsive to treated with NF-κB inhibitors.

Other Therapeutic Utilities

Since NF-κB plays a pivotal role in the coordinated transactivation of cytokine and adhesion molecule genes involved in atherosclerosis and lesion formation after vascular injury (Yoshimura et al., *Gene Therapy* 8: 1635-1642 (2001)); neuronal damage after cerebral ischemia (Ueno et al., *J. Thoracic and Cardiovascular Surgery* 122(4): 720-727 (2001)); chronic airway inflammation (Griesenbach et al., *Gene Therapy* 7, 306-313 (2000)); progression of autoimmune myocarditis (Yokoseki et al., *Circ. Res.* 89: 899-906 (2001)); acute rejection and graft arteriopathy in cardiac transplantation (Suzuki et al., *Gene Therapy* 7: 1847-1852 (2000)); and myocardial infarction (Morishita et al., *Nature Medicine* 3(8): 894-899 (1997)), NF-κB decoy molecules also find utility in the treatment of such diseases and conditions.

Recent evidence indicates that NF-κB and the signaling pathways that are involved in its activation are also important for tumor development. See, e.g. Karin et al., *Nat. Rev. Cancer* 2(4):301-10 (2002). Therefore, blocking NF-κB by the decoy molecules of the present invention finds utility in the prevention and treatment of cancer, offering a new anti-cancer strategy, either alone or in combination with other treatment options.

Delivery of the NF-κB dsODN Molecules

The route of delivery of the NF-κB decoys of the present invention depends on the disease or pathological condition the prevention and/or treatment is targeted. For certain indications, a preferred mode of delivering the NF-κB decoys of the present invention is pressure-mediated transfection, as described, for example, in U.S. Pat. Nos. 5,922,687 and 6,395,550, the entire disclosures of which are hereby expressly incorporated by reference. In brief, the NF-κB decoy molecules are delivered to cells in a tissue by placing the decoy nucleic acid in an extracellular environment of the cells, and establishing an incubation pressure around the cells and the extracellular environment. The establishment of the incubation pressure facilitates the uptake of the nucleic acid by the cells, and enhances localization to the cell nuclei.

More specifically, a sealed enclosure containing the tissue and the extracellular environment is defined, and the incubation pressure is established within the sealed enclosure. In a preferred embodiment, the boundary of the enclosure is defined substantially by an enclosing means, so that target tissue (tissue comprising the target cell) is subjected to isotropic pressure, and does not distend or experience trauma. In another embodiment, part of the enclosure boundary is defined by a tissue. A protective means such as an inelastic sheath is then placed around the tissue to prevent distension and trauma in the tissue. While the incubation pressure depends on the application, incubation pressures about 300 mmHg-1500 mmHg above atmospheric pressure, or at least about 100 mmHg above atmospheric pressure are generally suitable for many applications.

The incubation period necessary for achieving maximal transfection efficiency depends on parameters such as the incubation pressure and the target tissue type. For some tissue, such as human vein tissue, an incubation period on the order of minutes (>10 minute) at low pressure (about 0.5 atm) is sufficient for achieving a transfection efficiency of 80-90%. For other tissue, such as rat aorta tissue, an incubation period on the order of hours (>1 hour) at high pressure (about 2 atm) is necessary for achieving a transfection efficiency of 80-90%.

Suitable mammalian target tissue for this type of delivery includes blood vessel tissue (in particular veins used as grafts in arteries), heart, bone marrow, and normal and tumor connective tissue, liver, genital-urinary system, bones, muscles, gastrointestinal organs, endocrine and exocrine organs, synovial tissue and skin. A method of the present invention can be applied to parts of an organ, to a whole organ, or to a whole organism. In one embodiment a nucleic acid solution can be perfused into a target region (e.g. a kidney) of a patient, and the patient is subject to pressure in a pressurization chamber.

For other applications, the NF-κB decoys of the present invention can be administered by other conventional techniques. For example, retroviral transfection, transfection in the form of liposomes are among the known methods suitable for transfection. For details see also Dzau et al., *Trends in Biotech* 11:205-210 (1993); or Morishita et al., *Proc. Natl. Acad. Sci. USA* 90:8474-8478 (1993). When administered in liposomes, the decoy concentration in the lumen will generally be in the range of about 0.1 µM to about 50 µM per decoy, more usually about 1 µM to about 10 µM, most usually about 3 µM.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides. In general, an effective dose is from 0.01 µg to 100 g per kg of body weight. Persons of ordinary skill in the art can easily estimate repetition rates for dosing based on measured residence times and concentrations of the drug in bodily fluids or tissues. In addition to the potency of the specific decoy molecule delivered, the effective dose will depend on the target disease, the route of delivery, the formulation used, the severity of the disease, the age, sex, and overall condition of the patient to be treated, and other similar considerations.

For treatment of rheumatoid arthritis and inflammatory bowel disease (IBD), murine experiments typically use about 25-100 µg decoy in 50 to 100 µl injectable formulation. Based on these dose regimens, determination of the proper dosage for other species, including humans, can be assisted by mathematical calculations that have been developed for inter-species scaling. See, for example, Mordenti et al., *Pharm Res* 8:1351-9 (1991).

For topical application, the decoys of the present invention are administered in the form of conventional topical formulations, such as, for example, creams, ointments, gels, suspensions, and the like. Preferably, such topical formulations will contain one or more penetration enhancers and/or surfactants to assure efficient delivery through the skin. Topical formulations for delivery of dsODN molecules are described in co-pending application U.S. Provisional Application Ser. No. 60/612,046, filed on Sep. 21, 2004, the entire disclosure of which is hereby expressly incorporated by reference. Topical formulations specifically include aqueous, emulsion-based and liposome formulations. For the treatment of dermatitis/eczema, a typical formulation may be a topical cream containing about 0.1 to 5% by weight, or about 0.2 to 3% by weight, or about 0.25 to 1% by weight of active ingredient. In order to increase half-life, for dermatological applications, at least one and preferably both strands of the NF-κB decoy molecules of the present invention are fully phosphorothioated.

For other delivery routes, the most suitable concentration can be determined empirically. The determination of the appropriate concentrations and doses is well within the competence of one skilled in the art. Optimal treatment parameters will vary depending on the indication, decoy, clinical status of the patient, etc., and can be determined empirically based on the instructions provided herein and general knowledge in the art.

The decoys may be administered as compositions comprising individual decoys or mixtures of decoys. Usually, a mixture contains up to 6, more usually up to 4, more usually up to 2 decoy molecules.

Many anti-inflammatory and anti-rheumatic drugs, including glucocorticoids, aspirin, sodium salicylate, and sulfosalazine, are inhibitors of NF-κB activation. For the treatment of inflammatory and autoimmune diseases and conditions, the NF-κB decoy molecules of the present invention can optionally be administered in combination with such drug treatments. Combination treatment includes simultaneous administration as well as consecutive administration of two or more drugs in any order. Thus, for example, the topical anti-inflammatory applications, the NF-κB decoys of the invention can be administered in combination with betamethasone or similar therapeutic agents.

In cancer therapy, the administration of the NF-κB decoy molecules can be combined with other treatment options, including treatment with chemotherapeutic anticancer agents and/or radiation therapy.

Further details of the invention will be apparent from the following non-limiting Examples.

EXAMPLE 1

Design and Testing of NF-κB Decoy Molecules

Design

NF-κB dsODN decoy molecules were designed and tested for their ability to bind and/or compete for binding of NF-κB. In a particular aspect, the goal of the invention was to design NF-κB decoy molecules that preferentially bind p65/p50 and/or cRel/p50 heterodimers over p50/p50 homodimers. As a result of not blocking p50/p50 homodimers, the selective decoy molecules of the invention allow these homodimers to block the promoters of NF-κB regulated genes, which provides an additional level of negative regulation of gene transcription.

In designing the oligonucleotide decoys, information available from crystal structure studies and computational analysis of the known NF-κB binding sites were utilized.

As discussed above, based on study of the crystal structure of the p50/p65 heterodimer bound to the immunoglobulin light-chain gene, which contains the consensus sequence of 5'-GGGACTTTCC-3' (SEQ ID NO: 2), it has been shown that p50 contacts the 5-base-pair subsite 5'-GGGAC-3' (SEQ ID NO: 3) and that p65 contacts the 4-basepair subsite 5'TTCC-3' (SEQ ID NO: 4). A series of NF-κB oligonucleotide decoys were designed, which contained fewer numbers of G's at the 5' end of the consensus binding site with the aim to prepare decoy molecules that would have lower affinity for the p50/p50 homodimer but still bind the p65/p50 heterodimer. These oligonucleotide decoys were assigned "core" and "flank" letter codes for ease of identification and presentation. The cores were assigned letter codes "A" through "L" and the flanks "T" through "Z". The decoys were tested in the gel shift assay to determine their ability to compete with a high affinity radiolabeled oligonucleotide for NF-κB binding The NF-κB-binding DNA consensus sequences were selected from publications of NF-κB related DNA-protein interactions, including: Blank et al., *EMBO J.* 10:4159-4167 (1991); Bours et al. *Mol. Cell. Biol.* 12:685-695 (1992); Bours et al. *U. Cell* 72:729-739 (1993); Duckett et al. *Mol. Cell. Biol.* 13:1315-1322 (1993); Fan C.-M., Maniatis T., *Nature* 354:395-398 (1991); Fujita et al., *Genes Dev.* 6:775-787 (1992); Fujita et al. *Genes Dev.* 7:1354-1363 (1993); Ghosh et al., *Nature* 373:303-310 (1995); Ghosh et al., *Cell* 62:1019-1029 (1990); Grumont et al., *Mol. Cell. Biol.* 14:8460-8470 (1994); Henkel et al., *Cell* 68:1121-1133 (1992); Ikeda et al. *Gene* 138:193-196 (1994); Kunsch et al., *Mol. Cell. Biol.* 12:4412-4421 (1992); LeClair et al., *Proc. Natl. Acad. Sci.* USA 89:8145-8149 (1992); Li C.-C. et al., *J. Biol. Chem.* 269:30089-30092 (1994);

Matthews et al., *Nucleic Acids Res.* 21:1727-1734 (1993); Mueller et al., *Nature* 373:311-317 (1995); Neri et al., *Cell* 67:1075-1087 (1991); Nolan et al., *Cell* 64:961-969 (1991); Paya et al., *Proc. Natl. Acad. Sci. USA* 89:7826-7830 (1992); Plaksin et al., *J. Exp. Med.* 177:1651-1662 (1993); Schmid et al., *Nature* 352:733-736 (1991); Schmitz M. L., Baeuerle P. A. *EMBO J.* 10:3805-3817 (1991); Ten et al., *EMBO J.* 11:195-203 (1992); Toledano et al., *J. Mol. Cell. Biol.* 13:852-860 (1993); Urban et al., *EMBO J.* 10:1817-1825 (1991).

Based on this available information, we generated a set of decoys for initial screening. These decoys include a "muta-tion decoy", the scrambled decoys, decoys with different length at their 5' or 3' end, and decoys with alternative base composition within the core region and/or in the flanking sequences.

To better understand the base-composition near the core binding sites of NF-κB, the core binding sites were computationally aligned (forward strand only) with known binding sequences. Based on this alignment, several major groups of decoys with slightly different core binding sites were created.

The major core and flanking sequences are listed in Table 1.

TABLE 1

| LETTER CODE | CORE | SEQ ID | LETTER CODE | FLANK | |
|---|---|---|---|---|---|
| A | GGGACTTTCC | 5 | T | CCTTGAA . . . TCC | (SEQ ID NO: 6 and SEQ ID NO: 8) |
| B | GGGGACTTTCC | 7 | U | AT . . . GT | (SEQ ID NO: 12 and SEQ ID NO: 14) |
| C | GGGGACTTTCCC | 9 | V | TC . . . TC | (SEQ ID NO: 16 and SEQ ID NO: 18) |
| D | GGGATTTCC | 11 | W | CTC . . . TGT | (SEQ ID NO: 20 and SEQ ID NO: 22) |
| E | GGACTTTCC | 13 | W' | CTC . . . TCA | (SEQ ID NO: 82 and SEQ ID NO: 83) |
| F | GACTTTCC | 15 | X | CT . . . TC | (SEQ ID NO: 84 and SEQ ID NO: 85) |
| G | GACTTTCCC | 17 | Y | TC . . . CA | (SEQ ID NO: 86 and SEQ ID NO: 87) |
| H | GGATTTCC | 19 | Z | AGTTGA . . . AGGC | (SEQ ID NO: 79 and SEQ ID NO: 88) |
| I | GGATTTCCC | 21 | Z' | TTGA . . . AGGC | (SEQ ID NO: 80 and SEQ ID NO: 89) |
| J | GATTTCC | 23 | Z-4 | TTGA . . . AG | (SEQ ID NO: 90 and SEQ ID NO: 91) |
| K | GATTTCCC | 24 | Z-2 | GTTGA . . . AGG | (SEQ ID NO: 81 and SEQ ID NO: 92) |
| L | GGACTTTCCC | 25 | | | |

Electrophoretic Mobility Shift Assay (EMSA)

The EMSA assay was employed to characterize oligonucleotide decoys for the NF-κB transcription factor. Using a radiolabeled oligonucleotide probe (non-mammalian, based on NF-κB promoter from HIV, sequence 113/114, SEQ ID NO: 48, and its complement), which exhibits high affinity for relevant members of the NF-κB family, binding of p65/p50, cRel/p50 and p50/p50 was tested using a nuclear extract from an activated monocyte cell line. Using the above modified oligonucleotides to compete for binding for the above-mentioned NF-κB family members, it was possible to compare the binding affinity of these oligonucleotides against the high affinity radiolabeled probe and each other. This assay has also enabled the design of a decoy which selectively binds particular members of the NF-κB family. By using increasing concentrations of various oligonucleotides, it was observed that, by deleting or changing targeted residues in the binding site, it was possible to specifically decrease the binding of the decoy molecule to p50/p50 homodimers, while retaining the affinity for p65/p50 and cRel/p50 heterodimers.

The NF-κB gel shift assays (EMSA) were performed as follows. A double-stranded oligonucleotide containing a consensus NF-κB binding site (5'AGTTGAGGG-GACTTTCCCAGGC 3') (SEQ ID NO: 78) was end-labeled with $\gamma^{32}$P-ATP using T4 Polynucleotide Kinase (Promega). One microgram of a nuclear extract prepared from LPS stimulated THP-1 cells (human monocyte cell line) was incubated with 35 fmol of radiolabeled probe in the presence or absence of competing unlabeled NF-κB double-stranded oligonucleotides (dsODN) or scrambled dsODN. The incubations were carried out at room temperature for 30 minutes in a 20 μl reaction volume composed of 10 mM Tris-HCl pH 8, 100 mM KCL, 5 mM MgCl2, 2 mM DTT, 10% Glycerol, 0.1% NP-40, 0.025% BSA and 1 μg Poly-dIdC. The reactions were loaded onto a 6% polyacrylamide gel, subjected to electrophoresis and dried. The dried gels were imaged and quantitated using a Typhoon 8600 PhosphorImager (Amersham) and ImageQuant software. The identity of the NF-κB proteins contained in complexes bound to the radiolabeled oligonucleotide probe were identified by pre-incubating the reactions for 5 minutes with individual antibodies specific for each member of the NF-κB family prior to the addition of the radiolabeled probe.

Nuclease Degradation and Chemistry Modifications

Native DNA is subject to rapid degradation inside of a cell, primarily through the action of 3' exonucleases, but also as a result of endonuclease attack. Therefore, oligonucleotide decoys are designed, they are modified to enhance their stability. Replacing one of the non-bridging oxygen atoms of the internucleotide linkage with a sulfur group, creating what is referred to as a phosphorothioate (PS) oligodeoxynucleotide, has been highly successful. The molecules are relatively nuclease resistant; however, they have been shown to exhibit nonspecific protein binding relative to 3'-terminally modified and unmodified oligonucleotide decoys (Brown et al, *J. Biol. Chem.* 269(43):26801-5 (1994)). Therefore, we performed a set of experiments to determine how many sulfurs were required at the 3', 5' or an internal site to provide nuclease resistance to our oligonucleotide decoys while maintaining the achieved specificity.

The Analysis of the EMSA Results

As discussed earlier, one goal of the work disclosed herein has been to develop NF-κB oligonucleotide decoy molecules that preferentially bind to the NF-κB p65/p50 and/or cRel/p50 heterodimer relative to the p50/p50 homodimer. The experimental results showed that the binding to p65/p50 and cRel/p50 were generally equivalent, therefore, only the p65/p50 bands were quantitated in our analysis.

Figure 2:
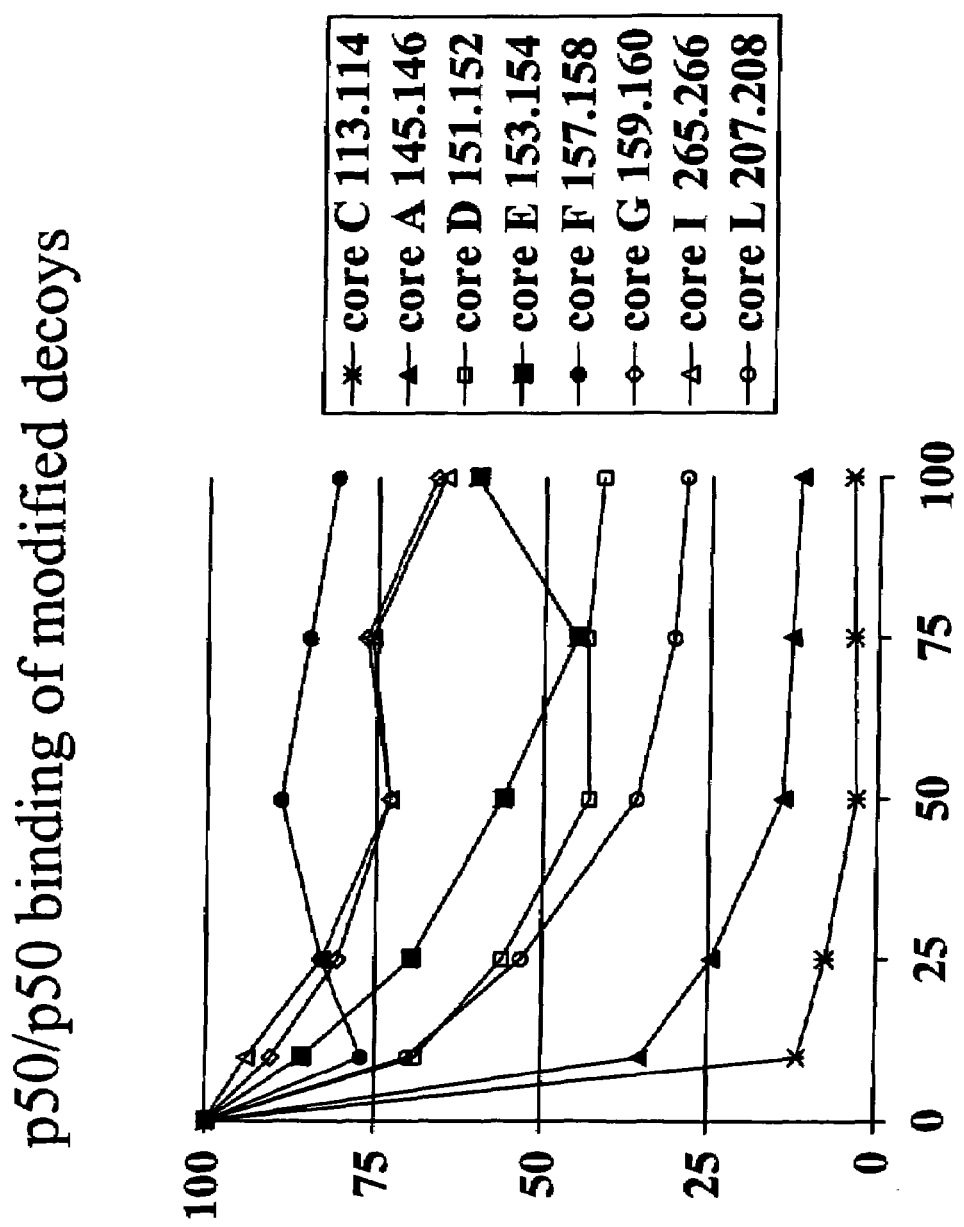
FIG. 2 is a graph showing the p50/p50 binding of certain NF-κB decoy molecules.

FIG. 1 shows the p65/p50 binding of certain NF-κB decoy molecules. FIG. 2 shows the p50/p50 binding of certain NF-κB decoy molecules.

Preferential binding was quantified using the specificity/affinity factor, calculated as follows:

$$\text{Specificy/affinity factor} = (S_{p50/p50} - S_{p65/p50}) \times S_{p50/p50} / S_{p65/p50}$$

where $S_{p50/p50}$ equals the molar excess of decoy required to compete 50% of the binding of p50/p50 to the non-mammalian NF-κB promoter from HIV (sequence 113/114) and $S_{p65/p50}$ equals the molar excess of decoy required to compete 50% of the binding of p65/p50 to the non-mammalian NF-κB promoter from HIV (sequence 113/114, where the reverse strand corresponding to sequence 113 is designated as "114"). The score (S) is assigned as 100 if the decoy is unable to compete at least 50% of the binding at any molar ratio tested.

A preferred decoy molecule will have a lower score for the p65/p50 heterodimer and a higher score for the p50/p50 homodimer. The specificity of the decoy to p65/p50 heterodimer versus p50/p50 homodimer is proportional to their difference of score (score p50/p50—score p65/50). The results of the EMSA competition binding experiments, performed as described above, are summarized in Table 2A, where the decoy molecules are listed starting with the most specific decoys (highest specificity/affinity factor).

TABLE 2A

| ID | Sequences | Core-Flank Alias | p65 | p50 | (p50 − p65) * p50 | (p50 − p65)/p65 | Specificity/affinity factor | SEQ ID NO |
|---|---|---|---|---|---|---|---|---|
| 173 | TTGAGGACTTTCCAG | E-Z-4 | 55 | 100 | 4500 | 0.82 | 81.82 | 26 |
| 177 | CTCGGACTTTCCTGT | E-W | 57.5 | 100 | 4250 | 0.74 | 73.9 | 27 |
| 151 | AGTTGAGGGATTTCCAGGC | D-Z | 36 | 69 | 2277 | 0.92 | 63.25 | 28 |
| 207 | AGTTGAGGACTTTCCCAGGC | L-Z | 20 | 45 | 1125 | 1.25 | 56.25 | 29 |
| 153 | AGTTGAGGACTTTCCAGGC | E-Z | 62.4 | 96 | 3225.6 | 0.54 | 51.69 | 30 |
| 265 | AGTTGAGGATTTCCCAGGC | I-Z | 54 | 84 | 2520 | 0.56 | 46.67 | 31 |
| 235 | TCGGACTTTCCCTC | L-V | 37 | 62.5 | 1593.75 | 0.69 | 43.07 | 32 |
| 117 | ATGGACTTTCCGT | E-U | 72.5 | 100 | 2750 | 0.38 | 37.93 | 33 |
| 227 | TCGGATTTCCTC | H-V | 74 | 100 | 2600 | 0.35 | 35.14 | 34 |
| 155 | TCGGACTTTCCTC | E-V | 81 | 97 | 1552 | 0.20 | 19.16 | 35 |
| 281 | TTGAGGACTTTCCAGGC | E-Z EVEN | 87 | 100 | 1300 | 0.15 | 14.94 | 36 |
| 121 | TCGGGACTTTCCTC | A-V | 25 | 34 | 306 | 0.36 | 12.24 | 37 |
| 263 | AGTTGAGGATTTCCAGGC | H-Z | 73 | 82 | 738 | 0.12 | 10.11 | 38 |
| 295 | TGAGGACTTTCCAGGCTC | | 92 | 100 | 800 | 0.09 | 8.70 | 39 |
| 289 | TGAGGACTTTCCAGGC | | 93 | 100 | 700 | 0.08 | 7.53 | 40 |

TABLE 2A-continued

| ID | Sequences | Core-Flank Alias | p65 | p50 | (p50 − p65) * p50 | (p50 − p65)/p65 | Specificity/ affinity factor | SEQ ID NO |
|---|---|---|---|---|---|---|---|---|
| 309 | CCTTGAAGGGATTTCCCTCC | M-T | 45 | 50 | 250 | 11 | 5.56 | 10 |
| 279 | TTGCGGACTTTCCAGGC | E-Z A->C EVEN | 48 | 52 | 208 | 0.08 | 4.33 | 41 |
| 191 | CTGGGACTTTCCTC | A-X | 19 | 22.5 | 78.75 | 0.18 | 4.14 | 42 |
| 141 | GTTGAGGGACTTTCCAGG | A-Z-2 | 7.5 | 10 | 25 | 0.33 | 3.33 | 43 |
| 123 | CTCGGGACTTTCCTGT | A-W | 8 | 10 | 20 | 0.25 | 2.50 | 44 |
| 195 | TCGGGACTTTCCCTC | C-V | 8.5 | 9 | 4.5 | 0.06 | 0.53 | 45 |
| 103 | CAGTAGTATGTGAGCCTGC | | 100 | 100 | 0 | 0.00 | 0.00 | 46 |
| 107 | TTGCCGTACCTGACTTAGCC | SCRAMBLED | 100 | 100 | 0 | 0.00 | 0.00 | 47 |
| 113 | AGTTGAGGGACTTTCCCAGGC | C-Z | 5 | 5 | 0 | 0.00 | 0.00 | 48 |
| 129 | TCGGATTTCCTC | D-V | 37.5 | 37.5 | 0 | 0.00 | 0.00 | 49 |
| 145 | AGTTGAGGGACTTTCCAGGC | A-Z | 8 | 8 | 0 | 0.00 | 0.00 | 50 |
| 157 | AGTTGAGACTTTCCAGGC | F-Z | 100 | 100 | 0 | 0.00 | 0.00 | 51 |
| 159 | AGTTGAGACTTTCCCAGGC | G-Z | 100 | 100 | 0 | 0.00 | 0.00 | 52 |
| 169 | GGACTTTCC | E | 100 | 100 | 0 | 0.00 | 0.00 | 53 |
| 171 | AGGACTTTCCA | E-A FLANK | 100 | 100 | 0 | 0.00 | 0.00 | 54 |
| 179 | CTGGACTTTCCTC | E-X | 100 | 100 | 0 | 0.00 | 0.00 | 55 |
| 183 | AAGAGGACTTTCCAGAG | E-AG FLANK | 100 | 100 | 0 | 0.00 | 0.00 | 56 |
| 185 | ATATGGACTTTCCTTAA | E-AT FLANK | 100 | 100 | 0 | 0.00 | 0.00 | 57 |
| 187 | CAACGGACTTTCCACAC | E-CA FLANK | 100 | 100 | 0 | 0.00 | 0.00 | 58 |
| 189 | CAGTGGACTTTCCACTG | E-CAGT FLANK | 100 | 100 | 0 | 0.00 | 0.00 | 59 |
| 213 | TCGACTTTCCCTC | G-V | 100 | 100 | 0 | 0.00 | 0.00 | 60 |
| 221 | CTGGGGACTTTCCCTC | C-X | 25 | 25 | 0 | 0.00 | 0.00 | 61 |
| 229 | TCGGATTTCCCTC | I-V | 100 | 100 | 0 | 0.00 | 0.00 | 62 |
| 231 | TCGATTTCCTC | J-V | 100 | 100 | 0 | 0.00 | 0.00 | 63 |
| 233 | TCGATTTCCTC | K-V | 100 | 100 | 0 | 0.00 | 0.00 | 64 |
| 239 | CTCGGGACTTTCCCTCA | C-W' | 9 | 9 | 0 | 0.00 | 0.00 | 65 |
| 241 | CTCGGACTTTCCTCA | E-W' | 100 | 100 | 0 | 0.00 | 0.00 | 66 |
| 273 | TTGAGGATTTCCAGGC | H-Z' (−3' 2 BP) | 100 | 100 | 0 | 0.00 | 0.00 | 67 |
| 275 | TTGAGGATTTCCAGGCT | H-Z' (−3' 1 BP) | 100 | 100 | 0 | 0.00 | 0.00 | 68 |
| 277 | TTGAGGATTTCCAGGCTC | H-Z' | 100 | 100 | 0 | 0.00 | 0.00 | 69 |
| 283 | TGAGGACTTTCCAGG | E-Z-3 | 100 | 100 | 0 | 0.00 | 0.00 | 70 |
| 285 | GAGGACTTTCCAG | E-Z-6 | 100 | 100 | 0 | 0.00 | 0.00 | 71 |
| 287 | GTTGAGGACTTTCCAGGC | | 100 | 100 | 0 | 0.00 | 0.00 | 72 |
| 291 | GAGGACTTTCCAGGC | | 100 | 100 | 0 | 0.00 | 0.00 | 73 |

TABLE 2A-continued

| ID | Sequences | Core-Flank Alias | p65 | p50 | (p50 - p65) * p50 | (p50 - p65)/p65 | Specificity/ affinity factor | SEQ ID NO |
|---|---|---|---|---|---|---|---|---|
| 293 | AGGACTTTCCAGGC | | 100 | 100 | 0 | 0.00 | 0.00 | 74 |
| 297 | AGGACTTTCCAGGCTC | | 100 | 100 | 0 | 0.00 | 0.00 | 75 |
| 259 | TTGAGGACTTTCCAGGCTC | E-Z' | 87 | 85 | -170 | -0.02 | -1.95 | 76 |
| 197 | CTCGGGGACTTTCCCTGT | C-W | 26 | 17.5 | -148.75 | -0.33 | -5.72 | 77 |

E-Z minus 4 is E-Z with the two 5' and 3' bases deleted
E-Z even is E-Z minus the two 5' bases
E-Z a to C Even is E-Z with the A in position 6 changed to a C
A-Z-2 is A-Z with the 5' and 3' bases deleted
E-A is the E core with an A added to the 5' and 3' ends
E-AG Flank is E core with AAGA as the 5' flank and AGAG as the 3' flank
E-AT Flank is E core with ATAT as the 5' flank and TTAA as the 3' flank
E-CA Flank is E core with CAAC as the 5' flank and ACAC as the 3' flank
E-CAGT Flank is E core with CAGT as the 5' flank and ACTG as the 3' flank
H-Z' (-3'2BP) is H-Z with the two 5' bases deleted
H-Z' (-3'1BP) is H-Z with two 5' bases deleted and a T added at the 3' end
E-Z-3 is E-Z with AGT deleted from the 5' end with C deleted from the 3' end
E-Z-6 is E-Z with AGTT deleted from the 5' end and GC deleted from the 3' end The data set forth in Table 2A suggest that the decoys with better p65/p50 specificity most likely share the "E" or "D" or "H" or "L" or "I" core sequence and "Z" or "W" or "V" or "U" or "Z-4" flanking sequences. In a more preferred group, the core sequence is "E" or "D" and the flanking sequence is "Z." The decoy designated 153/154 was chosen as best from the top few candidates with the consideration of other parameters (see below).

As discussed earlier, for certain uses of the NF-κB decoys herein specificity is not a requirement. For such applications, it is advantageous to select NF-κB decoy molecules with high binding affinity for p65. The following Table 2B shows the p65 binding affinity for some NF-κB decoy molecules tested.

TABLE 2B

| ID | Sequences | Core-Flank Alias | p65 | SEQ ID NO |
|---|---|---|---|---|
| 113 | AGTTGAGGGACTTTCCCAGGC | C-Z | 5 | 48 |
| 141 | GTTGAGGGACTTTCCAGG | A-Z-2 | 7.5 | 43 |
| 123 | CTCGGGACTTTCCTGT | A-W | 8 | 44 |
| 145 | AGTTGAGGGACTTTCCAGGC | A-Z | 8 | 50 |
| 195 | TCGGGGACTTTCCCTC | C-V | 8.5 | 45 |
| 239 | CTCGGGGACTTTCCCTCA | C-W' | 9 | 65 |
| 191 | CTGGGACTTTCCTC | A-X | 19 | 42 |
| 207 | AGTTGAGGACTTTCCCAGGC | L-Z | 20 | 29 |
| 121 | TCGGGACTTTCCTC | A-V | 25 | 37 |
| 221 | CTGGGACTTTCCCTC | C-X | 25 | 61 |
| 197 | CTCGGGGACTTTCCCTGT | C-W | 26 | 77 |
| 151 | AGTTGAGGGATTTCCAGGC | D-Z | 36 | 28 |
| 235 | TCGGACTTTCCCTC | L-V | 37 | 32 |
| 129 | TCGGGATTTCCTC | D-V | 37.5 | 49 |
| 309 | CCTTGAAGGGATTTCCCTCC | M-T | 45 | |
| 279 | TTGCGGACTTTCCAGGC | E-Z A->C EVEN | 48 | 41 |
| 265 | AGTTGAGGATTTCCCAGGC | I-Z | 54 | 31 |
| 173 | TTGAGGACTTTCCAG | E-Z-4 | 55 | 26 |
| 177 | CTCGGACTTTCCTGT | E-W | 57.5 | 27 |
| 153 | AGTTGAGGACTTTCCAGGC | E-Z | 62.4 | 30 |
| 117 | ATGGACTTTCCGT | E-U | 72.5 | 33 |
| 263 | AGTTGAGGATTTCCAGGC | H-Z | 73 | 38 |
| 227 | TCGGATTTCCTC | H-V | 74 | 34 |
| 155 | TCGGACTTTCCTC | E-V | 81 | 35 |
| 281 | TTGAGGACTTTCCAGGC | E-Z EVEN | 87 | 36 |
| 259 | TTGAGGACTTTCCAGGCTC | E-Z' | 87 | 76 |
| 295 | TGAGGACTTTCCAGGCTC | | 92 | 39 |
| 289 | TGAGGACTTTCCAGGC | | 93 | 40 |
| 103 | CAGTAGTATGTGAGCCTGC | | 100 | 46 |
| 107 | TTGCCGTACCTGACTTAGCC | SCRAMBLED | 100 | 47 |
| 157 | AGTTGAGACTTTCCAGGC | F-Z | 100 | 51 |
| 159 | AGTTGAGACTTTCCCAGGC | G-Z | 100 | 52 |
| 169 | GGACTTTCC | E | 100 | 53 |
| 171 | AGGACTTTCCA | E-A FLANK | 100 | 54 |
| 179 | CTGGACTTTCCTC | E-X | 100 | 55 |

TABLE 2B-continued

| ID | Sequences | Core-Flank Alias | p65 | SEQ ID NO |
|---|---|---|---|---|
| 183 | AAGAGGACTTTCCAGAG | E-AG FLANK | 100 | 56 |
| 185 | ATATGGACTTTCCTTAA | E-AT FLANK | 100 | 57 |
| 187 | CAACGGACTTTCCACAC | E-CA FLANK | 100 | 58 |
| 189 | CAGTGGACTTTCCACTG | E-CAGT FLANK | 100 | 59 |
| 213 | TCGACTTTCCCTC | G-V | 100 | 60 |
| 229 | TCGGATTTCCCTC | I-V | 100 | 62 |
| 231 | TCGATTTCCTC | J-V | 100 | 63 |
| 233 | TCGATTTCCCTC | K-V | 100 | 64 |
| 241 | CTCGGACTTTCCTCA | E-W' | 100 | 66 |
| 273 | TTGAGGATTTCCAGGC | H-Z' | 100 | 67 |
| 275 | TTGAGGATTTCCAGGCT | H-Z' | 100 | 68 |
| 277 | TTGAGGATTTCCAGGCTC | H-Z' | 100 | 69 |
| 283 | TGAGGACTTTCCAGG | E-Z-3 | 100 | 70 |
| 285 | GAGGACTTTCCAG | E-Z-6 | 100 | 71 |
| 287 | GTTGAGGACTTTCCAGGC | | 100 | 72 |
| 291 | GAGGACTTTCCAGGC | | 100 | 73 |
| 293 | AGGACTTTCCAGGC | | 100 | 74 |
| 297 | AGGACTTTCCAGGCTC | | 100 | 75 |

If increased p65 binding affinity is the goal, preferably decoys with an affinity score below 70, or below 60, or below 50, or below 40, or below 35, or below 30, or below 25, or below 20 are selected. Since this data was generated in a competitive binding assay, smaller scores indicate better binding affinity, as they represent the amount of competing material left binding after the competition. The data set forth in Table 2B suggests that decoys with high affinity for p65/p50 most likely share the "C" or "A" or "L" or "D" or "M" core sequence, and "Z" or "W" or "V" or "X" or "T" flanks. In a more preferred group, the core sequence is "C" and the flanking sequence is "Z". In another preferred group, the core sequence is "E" and the flanking sequence is "Z", and, preferably, the dsODN has a fully phosphorothioate backbone.

The Analysis of Chemical Modification of DNA Backbone

A similar analysis was applied to evaluate the chemical modification of DNA backbone for tested decoys.

TABLE 3A $S_{p50/p50}/S_{p65/p50}$ and specificy/affinity factor for 153/154 with various DNA backbones

| backbone | p65 | p50 | p50 – p65 | (p50 – p65) * p50 | (p50 – p65)/p65 | Specificity/ Affinity Factor |
|---|---|---|---|---|---|---|
| PO/H11 | 7.5 | 40 | 32.5 | 1300 | 4.33 | 173.33 |
| H7/H7 | 39 | 100 | 61 | 6100 | 1.56 | 156.41 |
| H6/H6 | 40 | 100 | 60 | 6000 | 1.50 | 150.00 |
| H3/H3 | 45 | 100 | 55 | 5500 | 1.22 | 122.22 |
| H11/PO | 7.5 | 33 | 25.5 | 841.5 | 3.40 | 112.20 |
| H5/H5 | 50 | 100 | 50 | 5000 | 1.00 | 100.00 |
| PO | 58 | 92 | 34 | 3128 | 0.59 | 53.93 |
| PO/H5 | 65 | 100 | 35 | 3500 | 0.54 | 53.85 |
| H8/H8 | 29 | 53 | 24 | 1272 | 0.83 | 43.86 |
| H10/H10 | 21 | 42 | 21 | 882 | 1.00 | 42.00 |
| H5/PO | 59 | 83 | 24 | 1992 | 0.41 | 33.76 |
| H10/H8 | 9 | 21 | 12 | 252 | 1.33 | 28.00 |
| H9/H9 | 17 | 30 | 13 | 390 | 0.76 | 22.94 |
| H4/H4 | 85 | 100 | 15 | 1500 | 0.18 | 17.65 |
| H8/H10 | 33 | 39 | 6 | 234 | 0.18 | 7.09 |
| H11/H11 | 24 | 27 | 3 | 81 | 0.13 | 3.38 |
| PS/PO | 5 | 5 | 0 | 0 | 0.00 | 0.00 |
| PO/PS | 5 | 5 | 0 | 0 | 0.00 | 0.00 |

In the foregoing Table 3A, where there are two designations for the backbone chemistry, the first one indicates the chemistry of strand 153 and the second the chemistry of strand 154. Fully phosphodiester bonds are designated "PO," fully phosphorothioate backbones are designated "PS." Hybrid backbones are designated with an "H" followed by the number of phosphorothioate backbone linkages, starting from the 3' end. Thus, H3 means that the three most 3' linkages are phosphorothioate and the rest of the backbone linkages are phosphodiester. If only one designation is shown (such as just PO), both strands have the same backbone chemistry.

The data set forth in Table 3A indicate that if either strand or both strands are fully phosphothioated (e.g. PS/PO or PO.PS) then the decoy has a high affinity for both p65/p50 and p50/p50, and therefore lacks the specificity desired. Generally, although not always, a higher number of phosphorothioate linkages resulted in reduced specificity. Generally, hybrid strands with more than 8 phosphorothioate linkages lacked specificity, whereas those with fewer than 7 retained acceptable affinity and specificity. However, H4/H4 has extremely low affinity, while H3/H3 and H5/H5 were both in the acceptable range. H11/PO and PO/H11 has good affinity and specificity. Based on half-life, specificity and affinity, H3/H3, H5/H5, H6/H6, and H7/H7 were identified as the optimal backbone for the 153/154 decoy. Optimal backbone chemistries for other decoys can be tested and determined in an analogous manner.

The effect of backbone chemistry on the p65 binding affinity is illustrated by the data set forth in Table 3B below.

TABLE 3B

| backbone | p65 |
|---|---|
| PS/PO | 5 |
| PO/PS | 5 |
| PS/PS | 5 |
| PO/H11 | 7.5 |
| H11/PO | 7.5 |
| H10/H8 | 9 |
| H9/H9 | 17 |
| H10/H10 | 21 |
| H11/H11 | 24 |
| H8/H8 | 29 |
| H8/H10 | 33 |
| H7/H7 | 39 |

TABLE 3B-continued

| backbone | p65 |
|---|---|
| H6/H6 | 40 |
| H3/H3 | 45 |
| H5/H5 | 50 |
| PO | 58 |
| H5/PO | 59 |
| PO/H5 | 65 |
| H4/H4 | 85 |

Just as before, if increased p65 binding affinity is the goal, preferably decoys with an affinity score below 40, or below 35, or below 30, or below 25, or below 20 are selected. Since this data was generated in a competitive binding assay, smaller scores indicate better binding affinity, as they represent the amount of competing material left binding after the competition. The results set forth in Table 3B show that, with a few exceptions, such as H4 on both strands or H5 on one strand, which decreases p65 binding affinity, increasing the level of phosphorothioate substitutions generally increases p65 binding affinity.

Specificity Relative to Other Transcription Factors

Figure 3:
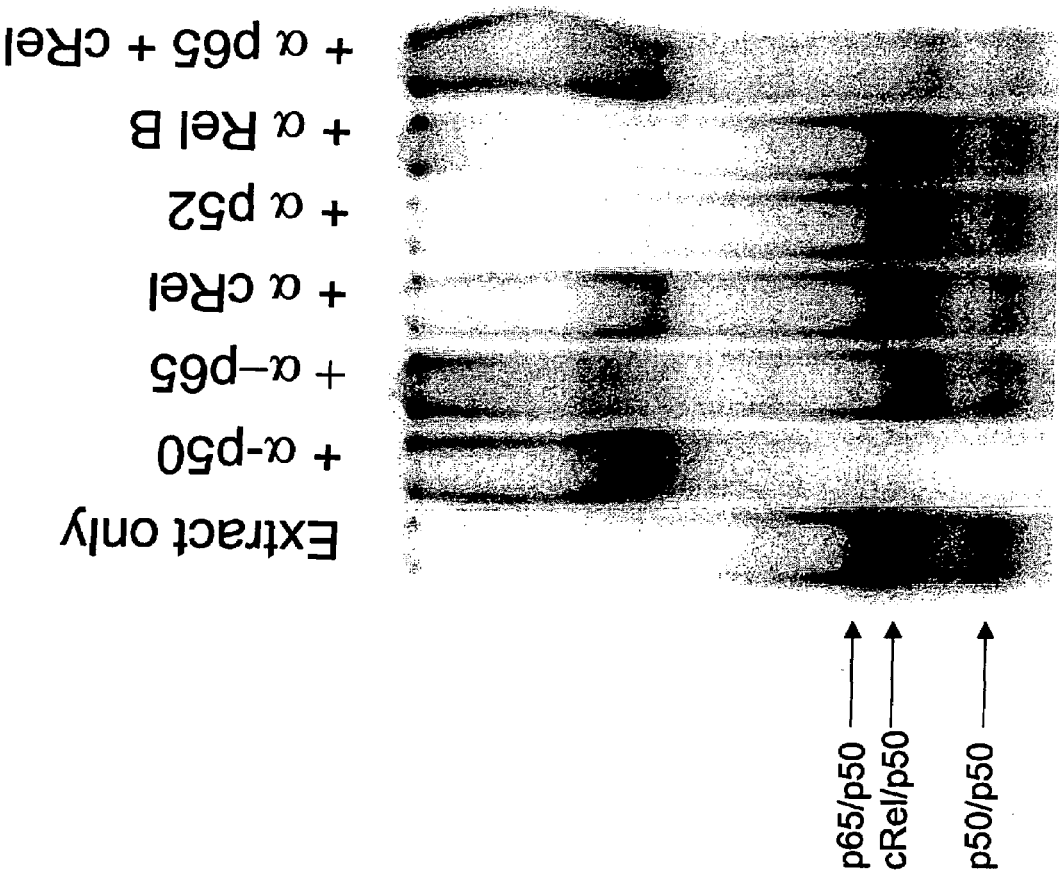
FIG. 3 shows quantitated results from EMSA assay. The ability of the decoy molecules designated "E" to compete non-specifically for binding of the transcription factor Oct-1 was tested. The Oct-1 decoy was radiolabeled in this assay. The amount of band remaining after addition of competitor is graphed. Bands were quantitated using a Typhoon Phosphorimager (Molecular Dynamics). The results indicate that the tested NF-κB decoy does not compete non-specifically for a promoter for which it has no specificity. The positive control was cold Oct-1 probe.

Decoy molecules must also specifically block only the target transcription factor and not non-specificially bind and block unrelated transcription factors. It has also been established that it is possible to design NF-κB decoy molecules which do not exhibit any non-specific effects on unrelated promoters using EMSA. Specifically, using radiolabeled oligonucleotide probes corresponding to the promoter sequences for the ubiquitous transcription factor Oct-1, it demonstrated that 153/154 (wherein "154" designates the reverse sequence corresponding to the sequence "153") PO and H3 NF-κB decoy did not show any binding affinity for the promoter (FIG. 3). This is important because any non-specific effects of an oligonucleotide to other important proteins in the cell could result in unwanted toxicity of the decoy for the treatment individual.

Half-life

Native DNA is subject to rapid degradation inside a cell, primarily through the action of 3' exonucleases, but also as a result of endonuclease attack. Therefore, when oligonucleotide decoys are designed, they are modified to enhance their stability. Replacing one of the non-bridging oxygen atoms of the internucleotide linkage with a sulfur group, creating what is referred to as a phosphorothioate oligodeoxynucleotide, has been highly successful. The molecules are relatively nuclease resistant; however, they have been shown to exhibit non-specific protein binding relative to 3'-terminally modified and unmodified oligonucleotide decoys (Brown et al., *J. Biol. Chem.* 269:26801-5 (1994)). Therefore, a set of experiments were performed to determine how many sulfurs were required at the 3'- or 5'-end, or at an internal site to provide nuclease resistance to the oligonucleotide decoys herein, while maintaining specificity.

Binding specificity was assessed by the gel shift assay described above. 3'-exonuclease resistance was assessed using a standard snake venom assay (Cummins et al., *Nucleic Acids Res.* 23:2019-24 (1995)). To assess the resistance of the decoys to more relevant mammalian nuclease activity, as assay was adapted in which cytoplasmic and nuclear extracts were prepared from activated macrophages. (Hoke et al., *Nucl. Acids Res.* 19(20):5743-8 (1991)). The activity of the extracts was confirmed with positive controls in each assay. It was determined that capping the 3'-ends of each strand of the decoy with a few sulfur groups was sufficient to protect it from nuclease degradation.

Together these data indicate that for a p50/p65-selective NF-κB decoy 3-5 sulfurs at the 3' ends of a 19-mer oligonucleotide duplex are sufficient to protect the decoy from nuclease degradation. Additionally, it was able to maintain specific subunit binding within the transcription factor family as well as lack of binding to irrelevant transcription factors. These data demonstrate that the present invention provides methods and means for designing specific and long-lasting oligonucleotide decoys targeting transcription factors, in particular NF-κB.

EXAMPLE 2

NF-κB Decoy Molecules Comprising a Nuclear Localization Signal

In order to determine the ability of a nuclear localization signal (NLS) containing peptide to improve the entry of an oligonucleotide decoy into the nucleus, a peptide with the NLS sequence based on the simian virus 40 large tumor antigen (PKKKRKVEDPYC) (SEQ ID NO:93) was synthesized by Sigma Genosys and conjugated to the NF-κB 153 H3 oligonucleotide as follows. Briefly, 6.5 nmols of oligonucleotide was first incubated with 40-fold molar excess of the linker Sulfo-SMCC (Pierce) at room temperature for 2 hours. After removal of excess linker from the reaction by a NAP-10 column (Pharmacia Biotech), the activated oligonucleotide was incubated with 5-fold molar excess of the NLS peptide at room temperature overnight. To assess the percentage of oligonucleotide successfully conjugated to the NLS peptide, the reaction was analyzed by loading 1 µl onto a 20% PAGE gel (non-denaturing). The gel was stained with SYBR Gold (Molecular Probes) and visualized on a Typhoon Phosphorimager (Amersham). The concentration of the NLS-peptide conjugated single strand 153 H3 was determined by OD absorbance. The conjugate was then annealed to its complemetary strand 154 H3 (in equal molar amounts) containing a biotin molecule at its 5' end. The presence of the biotin molecule on the now double stranded NLS decoy was to enable visualization (via streptavidin) of the localization through the use of microscopy.

The following examples describe results obtained by the administration of the NF-κB decoy "153/154." In the dermatological models, both strands of the NF-κB decoy 153/154 are fully phosphorothioated, i.e. the 153/154 molecule is "PS/PS."

EXAMPLE 3

NF-κB Decoy Reduces Ear Swelling in Murine Atopic Dermatitis

To determine the efficacy and effective dose range of NF-κB decoy in Dustmite Ag (Dp) induced contact dermatitis in NC/Nga mice.

Method

Dp Ag induced dermatitis was induced as previously described (Sasakawa, T et al., *Int Arch Allergy Immunol* 126:239-47 (2001); Sasakawa et al., *Int Arch Allergy Immunol* 133:55-63 (2004)). Briefly, Six week old male NC/Nga mice were injected intradermally with 5 µg of Dp extract (Greer Laboratories, Lenoir, N.C.) dissolved in saline on the ventral side of their right ears on days 0, 2, 4, 7, 9, and 11. Starting on day 11, the DP injected ear was topically treated 2 times a day for 10-12 days with 20 µl of vehicle, vehicle containing 0.25% or 0.1% NF-κB decoy or betamethasone as a control. The ear thickness was measured with an ear thickness gauge (Oditest, Dyer Inc) 24 hr after each intradermal injection or treatment.

Results

Figure 4:
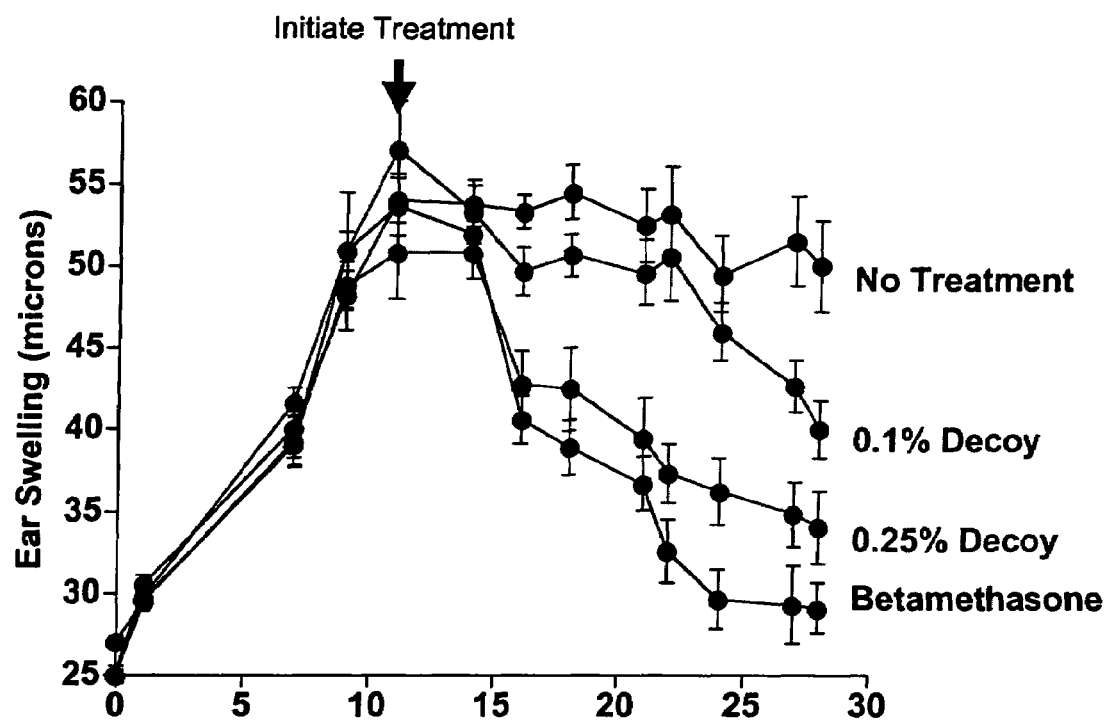
FIG. 4 that topical application of NF-κB decoy suppresses inflammation in a dose dependent manner in a mouse model of atopic dermatitis.

To examine the effect of NF-κB decoy treatment on established atopic dermatitis, we examined the ear swelling/inflammation as measured by ear thickness of Dp-injected NC/Nga mice with or without NF-κB decoy treatment. Dp extract was injected on the ventral side of the right ear on days 0, 2, 4, 7, 9, and 11. Topical NF-κB decoy was initiated on day 11 after the final Dp injection. Thickening of the ear injected with DP Ag was observed as early as 24 hours later and rapidly increased until day 11. Ear thickness was maintained for up to two weeks after the final Dp injection in both the untreated and vehicle treated ears. As shown in FIG. 4, topical 0.25% NF-κB decoy or betamethasone (B.I.D.) treatment resulted in a rapid decrease in ear thickness while the 0.1% NF-κB decoy treatment group resulted in little to no decrease in ear thickness similar to the vehicle control.

Conclusion

Topical application of NF-κB decoy suppresses inflammation in a dose dependent manner in this mouse model of atopic dermatitis.

EXAMPLE 4

Cessation of NF-κB Decoy Treatment Does Not Result in a Rebound of Ear Swelling and Inflammation in the Dp Injected Ear The purpose of this experiment was to determine whether or not NF-κB decoy efficacy is maintained when treatment is stopped.

Method

Dp Ag-induced dermatitis was induced as previously described (Sasakawa et al, supra). Briefly, six-week old male NC/Nga mice were injected intradermally with 5 µg of Dp extract (Greer Laboratories, Lenoir, N.C.) dissolved in saline on the ventral side of their right ears on days 0, 2, 4, 7, 9, and 11. Starting on day 11, the DP injected ear was topically treated 2 times a day for 10-12 days with 20 µl of vehicle, vehicle containing 0.25% NF-κB decoy or betamethasone as a control. Topical treatment was then stopped for 2 weeks. The ear thickness was measured with an ear thickness gauge (Oditest, Dyer Inc) 24 hr after each intradermal injection or treatment.

Results

Figure 5:
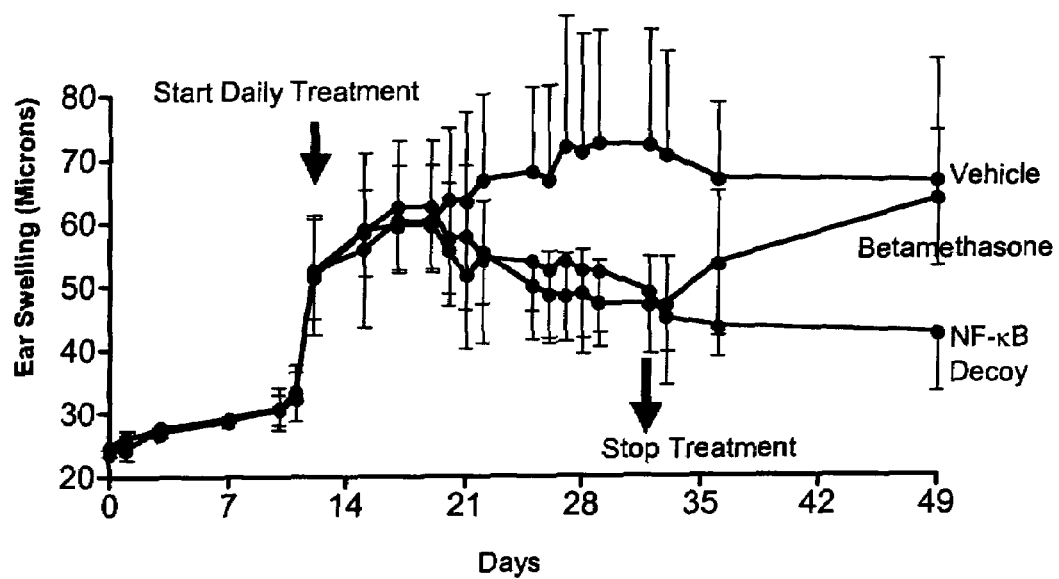
FIG. 5 shows that cessation of the betamethasone, but not NF-κB decoy treatment results in a rebound of ear swelling and inflammation in the Dp injected ear.

The ability of NF-κB decoy treatment to maintain the decrease in ear thickness after discontinuation of treatment was examined. As shown in FIG. 5, discontinuation of the NF-κB decoy treatment resulted in no increase in ear swelling, while the cessation of betamethasone in the Dp injected ears resulted in a significant increase of ear swelling.

Conclusion

Cessation of the betamethasone, but not NF-κB decoy treatment results in a rebound of ear swelling and inflammation in the Dp injected ear.

EXAMPLE 5

NF-κB Decoy Treatment Reduces Expression of Key Pro-inflammatory Genes in Dp Injected NC/Nga Mice The goal of this study was to evaluate the effect of NF-κB decoy treatment on elevated pro-inflammatory cytokine expression in Dp injected NC/Nga mice.

Method

Right ears of Dp-injected mice were removed 1 day after the final decoy treatment. Part of the ear was flash frozen in liquid nitrogen and store at −80° C. Total RNA was isolated from the ears using Qiazol (Qiagen) according to manufacturer's instruction. The expression of the mouse genes were assayed by real-time quantitative PCR with an ABI PRISM 7900 Sequence Detector System (Applied Biosystems, Foster City, Calif.). All procedures were carried out as previously described (Hurst et al., *Immunol* 169:443-53 (2002)). Briefly, Dnase-treated total RNAs were mixed with random hexamers (Gibco-BRL), Oligo dt (Boehringer), and the first strand cDNAs were synthesized with SurperScript II reverse transcriptase. Primers for the respective genes were designed using the primer design software Primer Express (Applied Biosystems). Primers were synthesized by Sigma Genosys (Woodlands, Tex.). The quantitative PCR was performed using TaqMan PCR reagent kits according to the manufacturer's protool (Applied Biosystems). Sample cDNAs equivalent to 25 ng of RNA were examined in each reaction in a 384-well PCR plate. Levels of ubiquitin were measured for each sample, and used as internal standard. Cytokine levels are expressed as relative expression to ubiquitin levels.

Results

Figure 6:
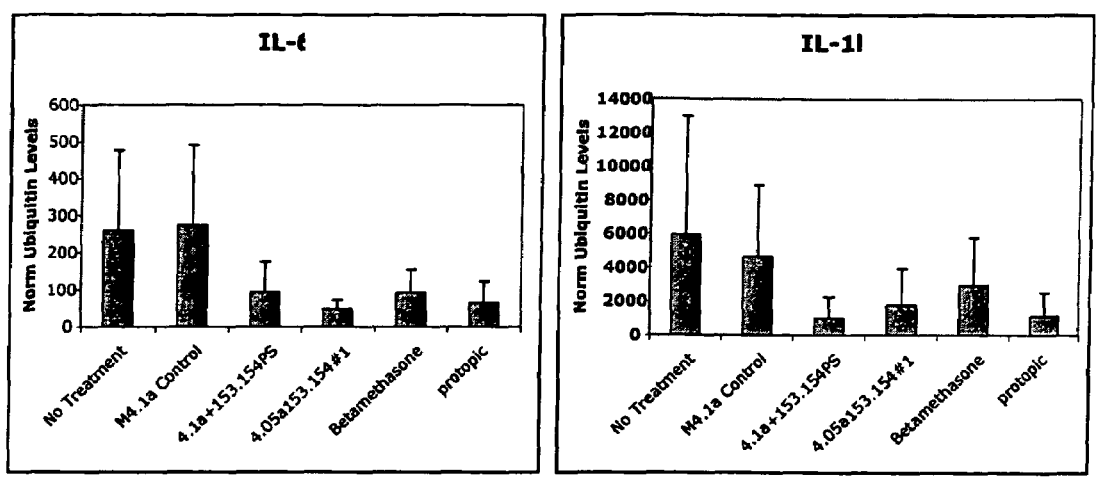
FIG. 6 shows that topical NF-κB decoy treatment decreases the expression of pro-inflammatory cytokines (IL-1B and IL-6) in Dp induced murine atopic dermatitis.

The effects of NF-κB decoy treatment on pro-inflammatory gene expression in the skin was analyzes by real-time quantitative PCR. As shown in FIG. 6, vehicle or non treated Dp injected mice showed a marked increase in expression levels of both IL-1β and IL-6, while NF-κB decoy treatment decreased the expression levels of both cytokines similar to that of protopic and betamethasone.

Conclusion

Topical NF-κB decoy treatment decreases the expression of pro-inflammatory cytokines (IL-1β and IL-6) in Dp induced murine atopic dermatitis.

EXAMPLE 6

The efficacy of NF-κB Decoy Therapy in Dustmite Ag (Dp) Induced Contact Dermatitis in NC/Nga Mice This experiment investigates the efficacy of NF-κB decoy in Dustmite Ag (Dp) induced contact dermatitis in NC/Nga mice.

Method

Right ears of Dp-injected mice were removed 1 day after the final decoy treatment. Part of the ear was fixed in 10% phosphate buffered formalin (pH 7.2) and embedded in paraffin, and 3 micron sections were cut. Then the samples were stained with hematoxylin and eosin for histology and toluidine blue for detection of degranulated mast cells.

Results

Figure 7:
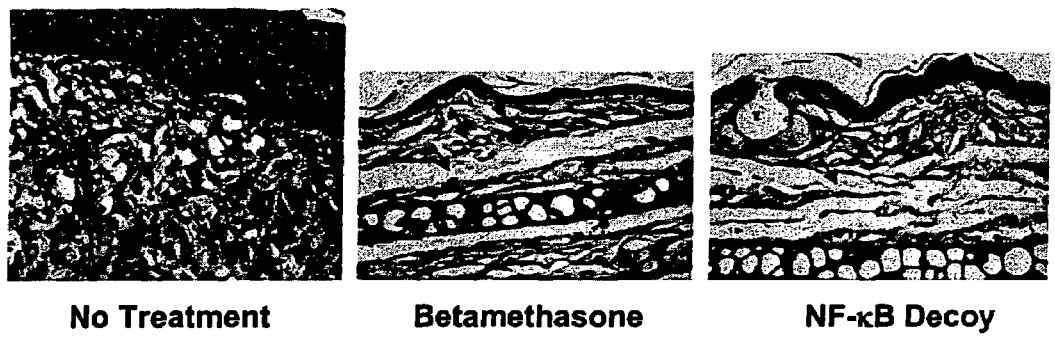
FIG. 7 shows that topical application of NF-κB decoy suppresses inflammation and the infiltration of inflammatory cells responsible for atopic dermatitis, and decreases epidermal hyperproliferation, cellular infiltration and degranulation of mast cells.

Histological examination of the skin lesions was performed on day 26. H&E staining showed severe epidermal hyperplasia and cellular infiltration into the dermis of vehicle treated ears injected with Dp, and treatment with NF-κB decoy or betamethasone produced both a decrease in epidermal hyperplasia and cellular infiltrate. As shown in FIG. 7, most of the mast cells in the Dp-injected, vehicle treated mice were degranulated while treatment with NF-κB decoy or betamethasone demonstrated a decrease in degranulated mast cells.

Conclusion

Topical application of NF-κB decoy suppresses inflammation and the infiltration of inflammatory cells (i.e mast cells) responsible for atopic dermatitis. Also, NF-κB decoy treatment decreased epidermal hyperproliferation, cellular infiltration and degranulation of mast cells.

EXAMPLE 7

Administration of NF-κB Decoy Into Arthritic Joints Led to Amelioration of Collagen-induced Arthritis In rheumatoid arthritis (RA) NF-κB plays a pivotal role in the development of arthritis. In the present experiment, it has been investigated whether local administration of an NF-κB decoy could suppress the severity of joint inflammation.

Method

Collagen Induced Arthritis (CIA) was induced using a method previously described by Trentham et al., *Arthritis Rheum* 25:911-6 (1982). Briefly, 6 week old female DA rats (Charles Rivers) were immunized intradermally with 1 mg of bovine type II collagen (Chondrex) dissolved in 0.5 ml of 0.1M acetic acid at 4° C. and emulsified in 0.5 ml of cold Freund's incomplete adjuvant (Difco, Detroit, Mich.). Onset of arthritis in the ankle joints could be seen between 10 and 12 days. All rats whose onset of arthritis could not be recognized visually by day 13 were excluded from the study. On day 14 after immunization, the rats were anesthetized with isoflurane. Next 50 μl of a 100 μg solution of NF-κB decoy was injected into the articular space of the hind ankle with a 27 gauge needle. As a control, 0.5 mg of prednisolone was injected into the articular space of the hind ankle. Footpad swelling was measured with a caliper every other day for the first 2 weeks then 1× week there after.

Results

Figure 8:
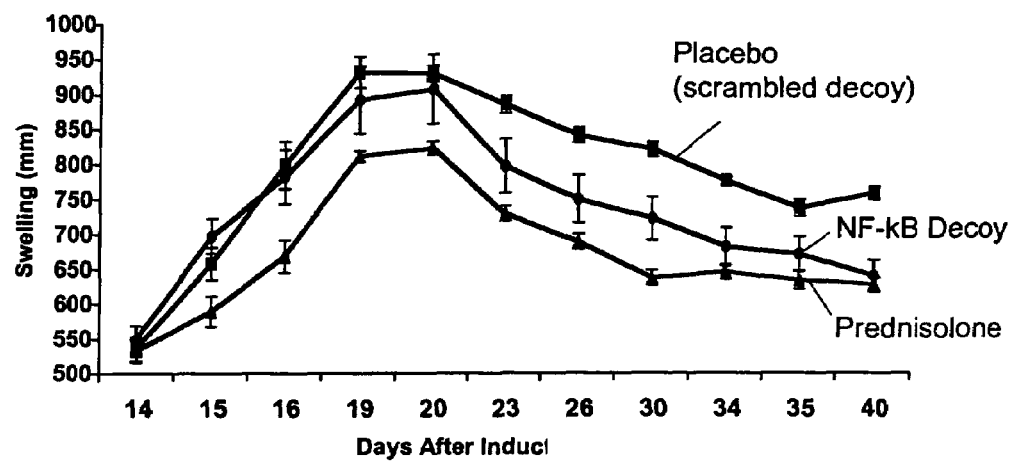
FIG. 8 shows that administration of NF-κB decoy into the arthritic joints of rats with collagen induced arthritis (CIA) leads to amelioration of arthritis.

Hindpaw swelling in CIA rats injected with NF-κB decoy was measured daily for the first week and then twice a week thereafter. As shown in FIG. 8, one-time injection of NF-κB decoy markedly reduced footpad swelling starting on day 23 and continued to resolve at a faster rate while the inflammation in the scramble control gradually decreased over time. Prednisolone treated animals significantly decreased hindpaw swelling almost immediately after injection and continued to suppress swelling throughout the experiment.

Conclusion

Administration of NF-κB decoy into the arthritic joints of CIA rats led to an amelioration of arthritis.

EXAMPLE 8

NF-κB Decoy Efficacy Studies in an Adjuvant Induced Arthritis (AIA) Model

The efficacy of NF-κB decoy in the prevention and treatment arthritis was further studied in the adjuvant induced arthritis (AIA) model of arthritis.

Method

AIA was induced using a method previously described by Taurog et al. (*Cell Immunol* 75:271-82 (1983); *Cell Immunol* 80:198-204 (1983)). Briefly, 7-8-week old female Lewis rats (Charles Rivers) were immunized intradermally at the base of the tail with 0.2 ml of a 10 mg/ml solution of Freund's adjuvant containing heat-killed mycobacterium tuberculosus H37Ra (Difco, Detroi, Mich.). Onset of arthritis in the ankle joints could be seen between 10 and 12 days. All rats whose unset of arthritis could not be recognized visually by day 12 were excluded from the study. On day 13 after immunization, the rats were anesthetized with isoflurane. Next 50 μl of a 100 μg solution of NF-κB decoy was injected into the articular space of the hind ankle with a 27 gauge needle. As a control, 0.5 mg of prednisolone was injected into the articular space of the hind ankle. Footpad swelling was measured with a caliper daily for the first week and 2 times a week thereafter.

Results

Figure 9:
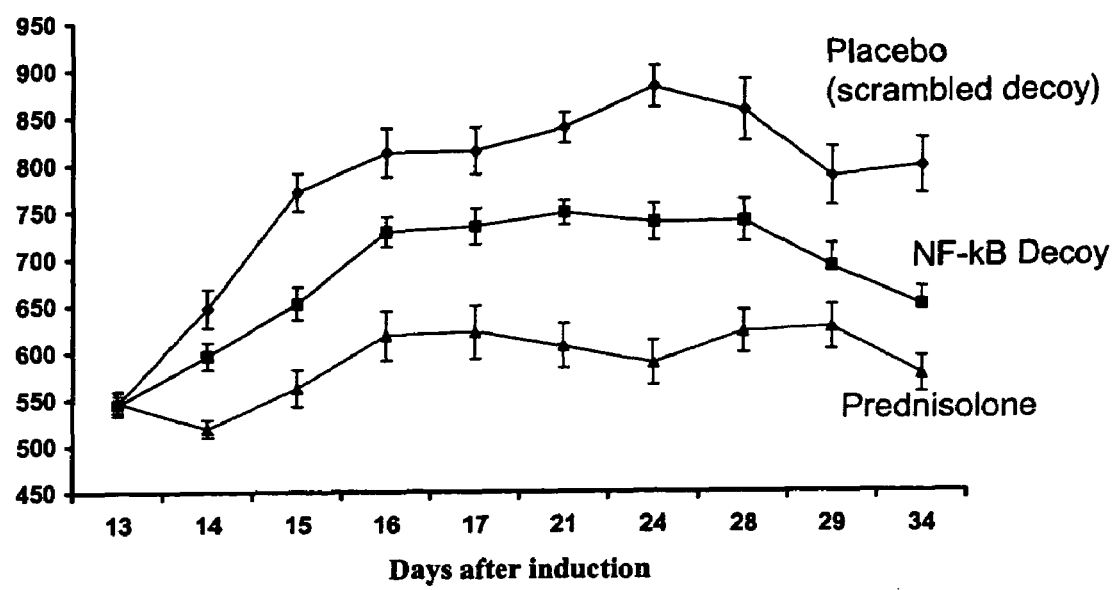
FIG. 9 shows that administration of NF-κB decoy into the arthritic joints of rats with adjuvant induced arthritis (AIA) leads to amelioration of arthritis.

The results shown in FIG. 9 show that local injection of the NF-κB decoy into the inflamed joint in this arthritis model markedly reduced footpad swelling and continued to ameliorate the swelling while in the footpad treated with the scramble decoy, swelling was greatly increased and maintained throughout the study. Prednisolone treatment severely inhibited the footpad swelling compared to that of the scramble decoy control.

EXAMPLE 9

NF-κB Decoy Efficacy Studies in the TNBS-induced Colitis Model

Trinitrobenzene sulfonic acid (TNBS)-induced colitis in the mouse is one of the most relevant animal models that resembles the etiology of Crohn's disease (CD) in humans. In this colitis model, intestinal inflammation develops as a result of the covalent binding of the haptenizing agent to autologous host proteins with subsequent stimulation of a delayed-type hypersensitivity to TNBS-modified self antigens. Although the relationship of this model to human disease is imperfect, the hapten-induced colitis displays CD-like features, notably transmural mononuclear inflammation and predominant Th-1 activity of the resident mucosal leukocytes. Inflammation and cytokine production in TNBS-treated mice, as well as in CD patients, is associated with activation of transcription factors such as nuclear factor NF-κB.

The procedures used for setting up the TNBS colitis model are very similar to that described in the following publications: Neurath et al., *Int Rev Immunol* 19:51-62 (2000); Bouma et al., *Gastroenterol* 123:554-565 (2002), and Bouma and Strober, *Nat Rev Immunol* 3:521-533 (2003).

In brief, according to this protocol under general anesthesia with isoflurane, colitis is induced in SJL/J mice by intrarectal administration of 2 mg TNBS in a 45% ethanol solution. Intrarectal injection is administered with a 3.5 F polyurethane umbilical catheter equipped with a 1-ml syringe. The catheter is inserted so that the tip is 3 cm proximal to the anal verge and the TNBS was injected with a total volume of 100 μl. To ensure distribution of the TNBS within the entire colon and cecum, mice are held in a vertical position for 30 s after the injection. Changes in body weight are monitored daily, which typically amount to weight losses of 15-30% occurring over a period of approximately 1-4 weeks after TNBS administration. The mice are treated with decoy in the same intrarectal manner with a single administration either prior to TNBS (prophylactic) or at various timepoints post TNBS induction (therapeutic). In some instances a second decoy treatment may be administered to prolong therapeutic effects if deemed necessary. In addition to body weight measurements, in certain experiments animals are sacrificed at different time points to harvest tissues for mRNA and/or protein expression and histological analysis.

Figure 10:
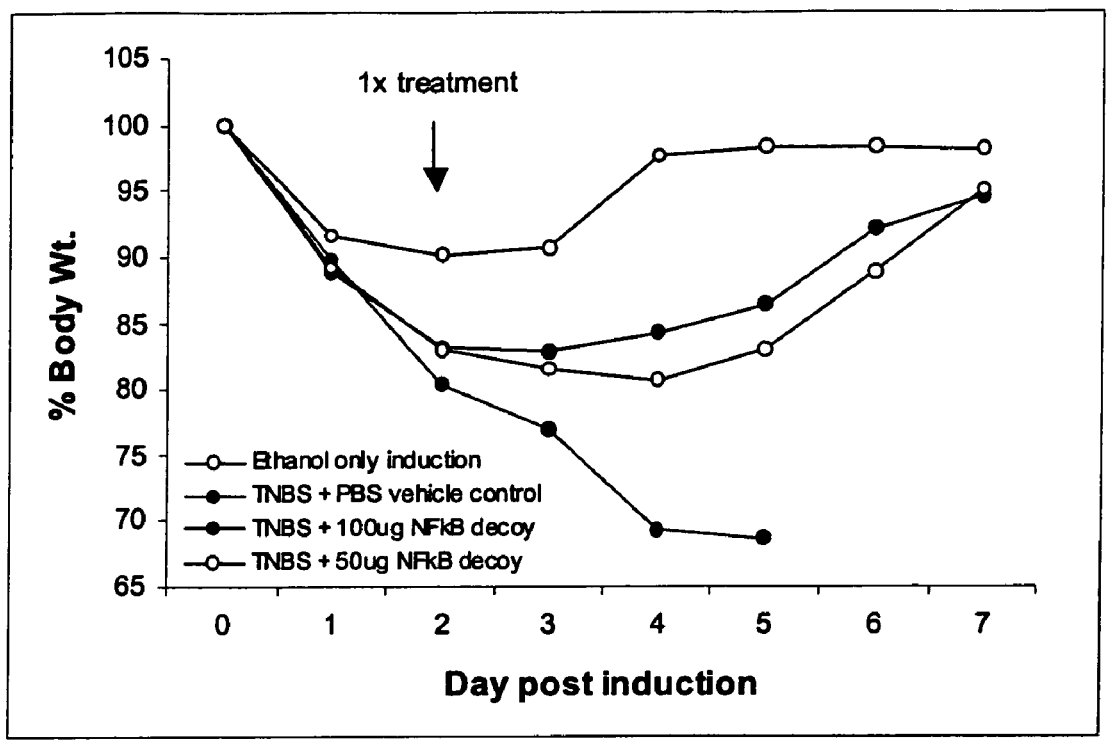
FIG. 10 shows that NF-κB decoy reverses weight loss in a murine model of TNBS-induced colitis.
Figure 11:
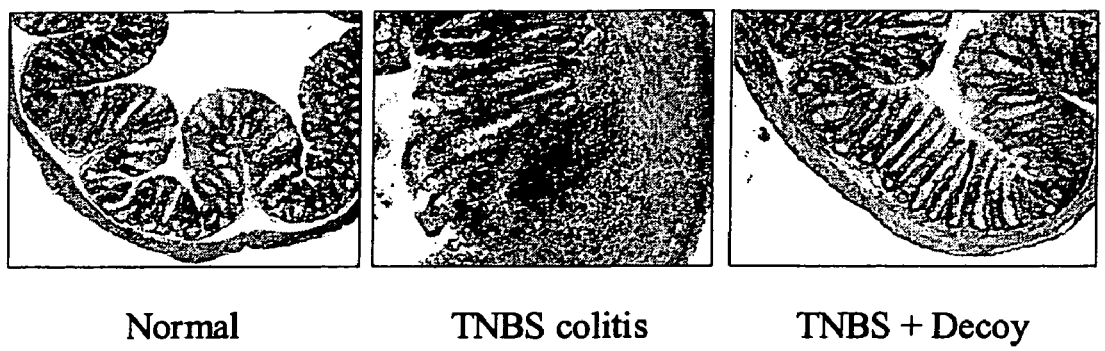
FIG. 11 shows that NF-κB decoy reduces inflammation in a murine model of TNBS-induced colitis.

Following this protocol, a single administration of NF-κB decoy given two days post disease induction can substantially reverse the weight loss associated with TNBS colitis (FIG. 10). Weight loss in this model is closely correlated with inflammation and disease severity. By day 2 post induction the mice have generally lost 15-20% body weight indicating disease onset. When vehicle alone was administered at this point, no ameliorative effects were seen and the mice in this group continued to lose weight and suffer from a high mortality rate. In treatment groups receiving either 50 or 100 μg NF-κB decoy on day 2, the disease associated weight loss was reversed very rapidly with almost complete recovery achieved by day 7. There was also a much higher survival rate in the decoy treated groups. The efficacy of NF-κB decoy was corroborated at the histopathological level in colons harvested from mice in both treatment groups at the day 7 post induction timepoint (FIG. 11). The TNBS-induced animals treated with vehicle alone showed localized inflammation, loss of the mucosal epithelium, an increase in crypt depth (with some sign of crypt branching), dissolution of the muscularis mucosae, and thickening of the muscularis layer (localized to the site of the inflammation). All these features are consistent with human inflammatory bowel disease (IBD) and the animal models presented in the literature. A single treatment with NF-κB decoy on day 2 post induction was able to reverse many of these pathological hallmarks of IBD.

EXAMPLE 10

NF-κB Decoy Efficacy Studies in the Oxazolone Colitis Model

A series of preclinical experiments have been initiated to evaluate the therapeutic potential of an NF-κB decoy of the present invention in inflammatory bowel disease. Oxazolone induced colitis in the mouse is a relevant model for studying disease pathology related to ulcerative colitis (UC) in humans. In this colitis model, intestinal inflammation develops as a result of covalent binding of the haptenizing agent to autologous host proteins with subsequent stimulation of a delayed-type hypersensitivity to oxazolone-mediated self antigens. Using the "classical" haptenazing agent, oxazolone elicits an inflammatory bowel disease involving the distal half of the colon, and has histologic features resembling UC rather than Crohn's disease. In addition, oxazolone colitis is driven by a Th2 as opposed to Th1 response. NF-κB regulates many of the cytokines, chemokines, and cell adhesion molecules contributing to this response.

The procedures used to set up this oxazolone colitis model were similar to those described by Neurath et al., *Int Rev Immunol* 19:51-62 (2000); Bouma et al., *Gastroenterol* 123:554-565 (2002), and Bouma and Strober, *Nat Rev Immunol* 3:521-533 (2003).

In brief, under general anesthesia with isoflurane, moce were presensitized by applying 200 μl of a 3% (w/v) solution of oxazolone (ethoxymethylene-2-phenyl-2-oxazolin-5-one) in 100% ethanol to a 2×2 cm field of shaved abdominal skin. Five days after presensitization, mice were rechallenged intrarectally with 150 μl of 1.5% oxazolone in 50% ethanol or only 50% ethanol, again under general anesthesia with isoflurane. Intrarectal injection was administered with a 3.5 F polyurethane umbilical catheter equipped with a 1-ml syringe. The catheter was inserted so that the tip was 3 cm proximal to the anal verge and the oxazolone was injected with a total volume of 150 μl. To ensure distribution of the oxazolone within the entire colon and cecum, mice were held in a vertical position for 30 seconds after the injection. Changes in body weight were monitored daily. Typically 15-20% weight losses were observed over a period of approximately 5-7 days after oxazolone administration. The oxazolone colitis model has an accurate disease progression from which the animals fully recover within 7-10 days.

The mice were treated with the NF-κB decoy in the same intrarectal manner with a single administration either prior to intrarectal oxazolone challenge (prophylactic) or at various time points post oxazolone challenge (therapeutic). In some instances, a second decoy treatment may be administered to prolong therapeutic effects if deemed necessary. In addition to body weight measurements, in certain experiments animals were sacrificed at various time points to harvest tissues for mRNA expression and histological analysis.

Figure 12:
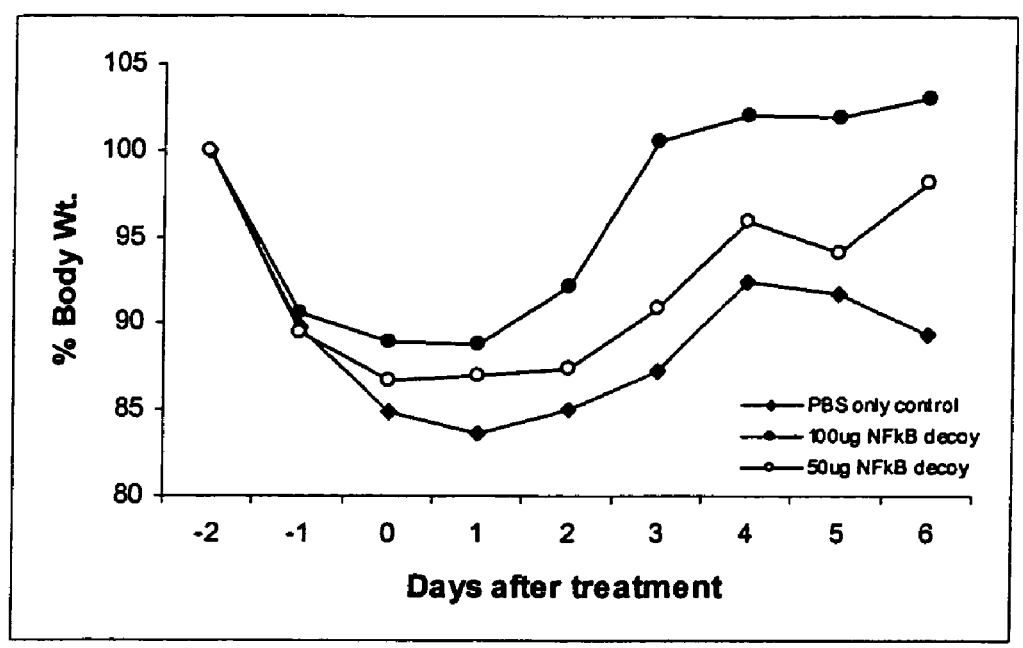
FIG. 12 shows that NF-κB decoy reverses weight loss in oxazolone-induced colitis.
Figure 13:
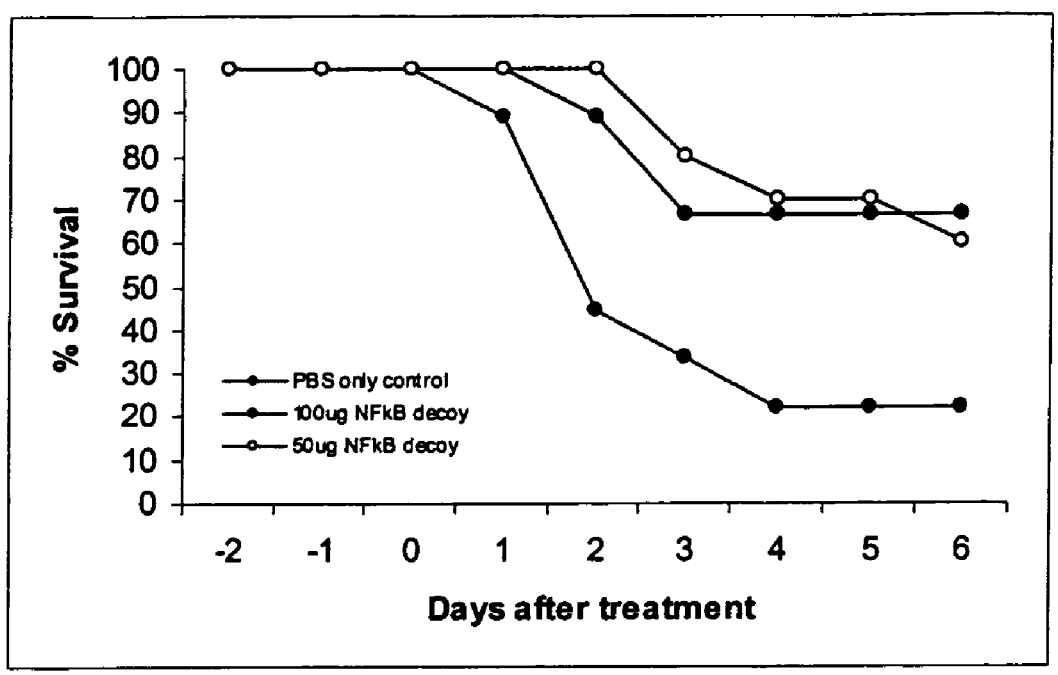
FIG. 13 shows that NF-κB decoy increases survival in oxazolone-induced colitis.

It has been found that a single administration of the NF-κB decoy given two days post disease induction could substantially reverse the weight loss associated with oxazolone colitis (FIG. 12). Weight loss in this model is closely associated with inflammation and disease severity. By day 2 post induction, the mice have generally lost 15-20% body weight indicating disease onset. When vehicle alone was administered at this point, no ameliorative effects were see, and the mice in this group continued to lose weight and suffer from a high mortality rate. In treatment groups receiving either 50 or 100 μg NF-κB decoy on day 2, the disease associated weight loss was reversed very rapidly with complete recovery observed in the 100 μg decoy group within 3 days of treatment. There was also a much higher survival rate in the decoy treatment groups (FIG. 13). By day 3, there was 60-70% mortality rate in the vehicle treated group. In contrast, in the treated groups there was only a 20-30% mortality rate.

All references cited throughout this disclosure are hereby expressly incorporated by reference.

Although the present invention is illustrated with reference to certain specific embodiments, it is not so limited. Modifications and variations are possible without diverting from the idea of the invention, and will be apparent to those skilled in the art. All such modifications and variations are specifically within the scope herein.

What is claimed is:

1. An NF-κB double-stranded decoy oligodeoxynucleotide (dsODN) molecule comprising a sense strand and an antisense strand, wherein the sense strand comprises the sequence of SEQ ID NO: 30.

2. The dsODN molecule of claim 1 wherein said antisense strand is at least partially complementary to said sense strand.

3. The dsODN molecule of claim 1 wherein said antisense strand is fully complementary to said sense strand.

4. The dsODN molecule of claim 1 having a phosphodiesterate backbone.

5. The dsODN molecule of claim 1 having a phosphorothioate backbone.

6. The dsODN molecule of claim 1 having a mixed phosphodiesterate-phosphorothioate backbone.

7. The dsODN molecule of claim 1 in which said sense and antisense strands are connected to each other solely by Watson-Crick base pairing.

8. The dsODN molecule of claim 1 wherein the sense strand consists of the sequence of SEQ ID NO: 30.

9. The dsODN molecule of claim 1 wherein the antisense strand comprises a sequence at least partially complementary to said sequence of SEQ ID NO: 30 within the sense strand.

10. The dsODN molecule of claim 1 wherein the antisense strand comprises a sequence fully complementary to said sequence of SEQ ID NO: 30 within the sense strand.

11. The dsODN molecule of claim 9 further comprising at least one single-stranded overhang.

12. The dsODN molecule of claim 9 wherein the sense and antisense strands are linked at the 5' and/or 3' end by a covalent bond, other than a peptide bond.

13. The dsODN molecule of claim 9 which is up to 28 base pairs long.

14. The dsODN molecule of claim 9 which is up to 24 base pairs long.

15. The dsODN molecule of claim 9 which is up to 22 base pairs long.

16. The dsODN molecule of claim 9 comprising modified nucleotides.

17. The dsODN molecule of claim 9 having a phosphodiester backbone.

18. The dsODN molecule of claim 9 having a phosphorothioate backbone.

19. The dsODN molecule of claim 9 having a mixed phosphodiester-phosphorothioate backbone.

20. The dsODN molecule of claim 9 which has a hybrid backbone.

21. The dsODN molecule of claim 20 wherein in said backbone, the three most 3' linkages are phosphorothioate bonds, and the rest of the linkages are phosphodiester bonds.

22. A composition comprising an NF-κB double-stranded oligodeoxynucleotide (dsODN) molecule of any one of claims 1 to 10.

23. The composition of claim 22 which is a pharmaceutical composition comprising said dsODN molecule in combination with a pharmaceutically acceptable carrier.

* * * * *

(12) EX PARTE REEXAMINATION CERTIFICATE (7760th)
United States Patent
McEvoy et al.

(10) Number: US 7,378,509 C1
(45) Certificate Issued: Sep. 21, 2010

(54) NF-KAPPAB OLIGONUCLEOTIDE DECOY MOLECULES

(75) Inventors: Leslie M. McEvoy, Mountain View, CA (US); Christi Parham, Menlo Park, CA (US); Jie Zhang, Campbell, CA (US); Rolf Ehrhardt, Mill Valley, CA (US)

(73) Assignee: Anesiva, Inc., South San Francisco, CA (US)

Reexamination Request:
No. 90/010,275, Sep. 11, 2008

Reexamination Certificate for:
Patent No.: 7,378,509
Issued: May 27, 2008
Appl. No.: 11/004,512
Filed: Dec. 2, 2004

Related U.S. Application Data

(60) Provisional application No. 60/526,623, filed on Dec. 2, 2003, and provisional application No. 60/612,029, filed on Sep. 21, 2004.

(51) Int. Cl.
*C07H 21/04* (2006.01)

(52) U.S. Cl. ...................................... 536/23.1
(58) Field of Classification Search ........... None
See application file for complete search history.

(56) References Cited

PUBLICATIONS

Pisate Kamthong & Ming–chi Wu, Inhibitor of nuclear factor–κB induction by cAMP antagonizes interleukin–1—induced human macrophage–colony–stimulating–factor expression, Biochem. J. (2001) 356:525–30.

Allard Kaptein et al. *Studies on the interaction between TWEAK and the death receptor WSL/TRAMP (DR3)*, FEBS Letters (2000) 485:135–41.

Frances Chen et al., *Crystal structure of p50/p65 heterodimer of transcription factor NF–κB bound to DNA*, Nature (1998) 391:410–13.

Charles Kunsch et al., *Selection of optimal κB/Rel DNA–binding motifs: Interaction of both subunits of NF–κB with DNA is required for transcriptional activation*, Mol. Cell. Bio. (1992) 12:4412–21.

Amy Roshak et al., *Manipulation of distinct NFκB proteins alters Interleukin–1β–induced human rheumatoid synovial fibroblast prostaglandin $E_2$ formation*, J. Biol. Chem. (1996) 271:31496–501.

M. Carey & S. Smale, Transcriptional Regulation in Eukaryotes: Concepts, Strategies, and Techniques, 257 (Cold Spring Harbor Laboratory, 1999).

*Primary Examiner*—Padmashri Ponnaluri

(57) ABSTRACT

The present invention concerns double-stranded NF-κB decoy oligodeoxynucleotide (NF-κB dsODN) molecules that contain a core sequence capable of specific binding to an NF-κB transcription factor. In a particular aspect, the invention concerns NF-κB decoy molecules that preferentially bind p50/p65 and/or cRel/p50 heterodimers over p50/p50 homodimers. In another aspect, the invention concerns NF-κB decoy molecules with improved binding affinity to p65.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

New claims 24–25 are added and determined to be patentable.

Claims 2-23 were not reexamined.

*24. The NF-κB double-stranded oligodeoxynucleotide molecule of claim 1, in an effective amount in combination with a cream, ointment or gel, formulated for topical administration to a subject for treating an inflammatory skin disease.*

*25. The NF-κB double-stranded oligodeoxynucleotide molecule of claim 1, in an effective amount in a needle suitable for injection of the oligodeoxynucleotide molecule into an inflamed joint in a subject for treating an arthritic disease.*

\* \* \* \* \*